United States Patent
Soerensen et al.

(10) Patent No.: US 11,124,808 B2
(45) Date of Patent: *Sep. 21, 2021

(54) SOLUBILIZATION OF MSW WITH BLEND ENZYMES

(71) Applicant: Renescience A/S, Fredericia (DK)

(72) Inventors: Hanne Risbjerg Soerensen, Holte (DK); Lisa Rosgaard, Valby (DK); Henrik B. Nielsen, Bagsværd (DK); Lone Baekgaard, Bagsværd (DK); Joanna Wawrzynczyk, Bagsværd (DK)

(73) Assignee: RENESCIENCE A/S, Fredericia (DK)

( * ) Notice: Subject to any disclaimer, the term of this patent is extended or adjusted under 35 U.S.C. 154(b) by 328 days.

This patent is subject to a terminal disclaimer.

(21) Appl. No.: 15/506,881

(22) PCT Filed: Aug. 27, 2015

(86) PCT No.: PCT/EP2015/069685
§ 371 (c)(1),
(2) Date: Feb. 27, 2017

(87) PCT Pub. No.: WO2016/030480
PCT Pub. Date: Mar. 3, 2016

(65) Prior Publication Data
US 2017/0240875 A1    Aug. 24, 2017

(30) Foreign Application Priority Data
Aug. 28, 2014 (EP) .................................. 14182698

(51) Int. Cl.
| | | |
|---|---|---|
| *C12P 7/10* | (2006.01) |
| *C12N 9/54* | (2006.01) |
| *C12N 9/42* | (2006.01) |
| *C12N 9/26* | (2006.01) |
| *C12N 9/24* | (2006.01) |
| *C12N 9/48* | (2006.01) |
| *C12N 9/88* | (2006.01) |
| *C12P 5/02* | (2006.01) |
| *C12P 7/08* | (2006.01) |
| *C11D 3/386* | (2006.01) |
| *C12N 9/20* | (2006.01) |

(52) U.S. Cl.
CPC ............ *C12P 7/10* (2013.01); *C11D 3/38618* (2013.01); *C11D 3/38627* (2013.01); *C11D 3/38645* (2013.01); *C12N 9/20* (2013.01); *C12N 9/244* (2013.01); *C12N 9/2411* (2013.01); *C12N 9/2434* (2013.01); *C12N 9/2448* (2013.01); *C12N 9/2488* (2013.01); *C12N 9/485* (2013.01); *C12N 9/54* (2013.01); *C12N 9/88* (2013.01); *C12P 5/023* (2013.01); *C12P 7/08* (2013.01); *C12Y 301/01* (2013.01); *C12Y 302/01* (2013.01); *C12Y 302/01006* (2013.01); *C12Y 302/01073* (2013.01); *C12Y 304/11001* (2013.01); *C12Y 304/21004* (2013.01); *C12Y 304/23023* (2013.01); *C12Y 304/23028* (2013.01)

(58) Field of Classification Search
CPC .......... C12P 7/08; C12P 7/10; C11D 3/38627; C11D 3/38645
See application file for complete search history.

(56) References Cited

U.S. PATENT DOCUMENTS

2010/0159536 A1*  6/2010  Sweeney ............... C12P 19/02
                                                     435/101

FOREIGN PATENT DOCUMENTS

| | | | |
|---|---|---|---|
| CN | 103890165 A | 6/2014 | |
| WO | WO 2007/044993 A2 | 4/2007 | |
| WO | WO 2012/093041 A1 | 7/2012 | |
| WO | WO 2012/101206 A2 | 8/2012 | |
| WO | WO 2013/016115 * | 1/2013 | ............. C12P 19/14 |
| WO | WO 2013/185777 A1 | 12/2013 | |
| WO | WO 2014/108454 A1 | 7/2014 | |

OTHER PUBLICATIONS

Kim et al., "Effect of Enzymatic pretreatment on acid fermentation of food waste", Journal of Chemical and Technology and Biotechnology, 2006, 81:974-980.*
Jensen et al., "Enzymatic processing of municipal solid waste", Waste Management, 2010, 30(12):2497-2503. doi: 10.1016/j.wasman.2010.07.009.*

* cited by examiner

*Primary Examiner* — Suzanne M Noakes
(74) *Attorney, Agent, or Firm* — McNeill Baur PLLC

(57) ABSTRACT

The present invention relates to a method for solubilisation or hydrolysis of Municipal Solid Waste (MSW) with an enzyme blend and an enzyme composition for solubilization of Municipal Solid Waste (MSW), the enzyme composition comprising a cellulolytic background composition and a protease, lipase and/or beta-glucanase.

21 Claims, 5 Drawing Sheets
Specification includes a Sequence Listing.

| Mix | Enzyme dose (%/TS) | Glucose | Xylose | Lactic acid | Sum | Glucose std. dev. | Xylose std. dev. | Lactic acid std. dev. | Sum std. Dev. |
|---|---|---|---|---|---|---|---|---|---|
| No enzyme | 0 | 0.3 | 0.1 | 5.8 | 6.2 | 0.0 | 0.0 | 0.3 | 0.4 |
| Blend enzymes 25% | 0.6 | 1.4 | 1.1 | 10.7 | 13.2 | 0.8 | 0.3 | 0.9 | 0.2 |
| Blend enzymes 50% | 1.2 | 4.9 | 1.9 | 10.0 | 16.8 | 0.4 | 0.1 | 0.2 | 0.4 |
| Blend enzymes 75% | 1.8 | 7.0 | 2.6 | 10.4 | 19.9 | 0.4 | 0.1 | 0.5 | 0.8 |
| Blend enzymes 100% | 2.4 | 7.9 | 2.5 | 9.9 | 20.3 | 0.5 | 0.2 | 0.4 | 0.9 |
| Blend enzymes 200% | 4.8 | 11.0 | 3.3 | 9.2 | 23.6 | 1.0 | 0.1 | 0.4 | 0.8 |
| CBC 25% | 0.6 | 0.4 | 0.7 | 11.1 | 12.3 | 0.0 | 0.3 | 0.2 | 0.5 |
| CBC 50% | 1.2 | 0.6 | 1.6 | 12.7 | 14.9 | 0.1 | 0.1 | 0.7 | 0.6 |
| CBC 75% | 1.8 | 1.0 | 2.1 | 13.8 | 17.0 | 0.1 | 0.1 | 0.4 | 0.5 |
| CBC 100% | 2.4 | 1.9 | 2.4 | 13.4 | 17.7 | 1.4 | 0.1 | 0.7 | 0.7 |
| CBC 200% | 4.8 | 4.4 | 3.1 | 14.6 | 22.1 | 0.5 | 0.2 | 0.3 | 0.8 |

FIG 5

SEQUENCE LISTING

```
<160> NUMBER OF SEQ ID NOS: 6

<210> SEQ ID NO 1
<211> LENGTH: 521
<212> TYPE: PRT
<213> ORGANISM: Bacillus amyloliquefaciens

<400> SEQUENCE: 1

Met Lys Lys Pro Leu Gly Lys Ile Val Ala Ser Thr Ala Leu Leu Ile
1               5                   10                  15
```

```
Ser Val Ala Phe Ser Ser Ile Ala Ser Ala Glu Asn Pro Gln
            20              25              30

Leu Lys Glu Asp Leu Thr Asn Phe Val Pro Lys His Ser Leu Val Gln
        35              40              45

Ser Glu Leu Pro Ser Val Ser Asp Lys Ala Ile Lys Gln Tyr Leu Lys
        50              55              60

Gln Asn Gly Lys Val Phe Lys Gly Asn Pro Ser Glu Arg Leu Lys Leu
65              70              75              80

Ile Asp Gln Thr Thr Asp Asp Leu Gly Tyr Lys His Phe Arg Tyr Val
                85              90              95

Pro Val Val Asn Gly Val Pro Val Lys Asp Ser Gln Val Ile Ile His
                100             105             110

Val Asp Lys Ser Asn Asn Val Tyr Ala Ile Asn Gly Glu Leu Asn Asn
            115             120             125

Asp Val Ser Ala Lys Thr Ala Asn Ser Lys Lys Leu Ser Ala Asn Gln
            130             135             140

Ala Leu Asp His Ala Tyr Lys Ala Ile Gly Lys Ser Pro Glu Ala Val
145             150             155             160

Ser Asn Gly Thr Val Ala Asn Lys Asn Lys Ala Glu Leu Lys Ala Ala
                165             170             175

Ala Thr Lys Asp Gly Lys Tyr Arg Leu Ala Tyr Asp Val Thr Ile Arg
                180             185             190

Tyr Ile Glu Pro Glu Pro Ala Asn Trp Glu Val Thr Val Asp Ala Glu
            195             200             205

Thr Gly Lys Ile Leu Lys Lys Gln Asn Lys Val Glu His Ala Ala Thr
210             215             220

Thr Gly Thr Gly Thr Thr Leu Lys Gly Lys Thr Val Ser Leu Asn Ile
225             230             235             240

Ser Ser Glu Ser Gly Lys Tyr Val Leu Arg Asp Leu Ser Lys Pro Thr
                245             250             255

Gly Thr Gln Ile Ile Thr Tyr Asp Leu Gln Asn Arg Glu Tyr Asn Leu
                260             265             270

Pro Gly Thr Leu Val Ser Ser Thr Thr Asn Gln Phe Thr Thr Ser Ser
            275             280             285

Gln Arg Ala Ala Val Asp Ala His Tyr Asn Leu Gly Lys Val Tyr Asp
290             295             300

Tyr Phe Tyr Gln Lys Phe Asn Arg Asn Ser Tyr Asp Asn Lys Gly Gly
305             310             315             320

Lys Ile Val Ser Ser Val His Tyr Gly Ser Arg Tyr Asn Asn Ala Ala
                325             330             335

Trp Ile Gly Asp Gln Met Ile Tyr Gly Asp Gly Asp Gly Ser Phe Phe
                340             345             350

Ser Pro Leu Ser Gly Ser Met Asp Val Thr Ala His Glu Met Thr His
            355             360             365

Gly Val Thr Gln Glu Thr Ala Asn Leu Asn Tyr Glu Asn Gln Pro Gly
            370             375             380

Ala Leu Asn Glu Ser Phe Ser Asp Val Phe Gly Tyr Phe Asn Asp Thr
385             390             395             400

Glu Asp Trp Asp Ile Gly Glu Asp Ile Thr Val Ser Gln Pro Ala Leu
                405             410             415

Arg Ser Leu Ser Asn Pro Thr Lys Tyr Gly Gln Pro Asp Asn Phe Lys
            420             425             430

Asn Tyr Lys Asn Leu Pro Asn Thr Asp Ala Gly Asp Tyr Gly Gly Val
```

```
                435                 440                 445
His Thr Asn Ser Gly Ile Pro Asn Lys Ala Ala Tyr Asn Thr Ile Thr
    450                 455                 460

Lys Ile Gly Val Asn Lys Ala Glu Gln Ile Tyr Tyr Arg Ala Leu Thr
465                 470                 475                 480

Val Tyr Leu Thr Pro Ser Ser Thr Phe Lys Asp Ala Lys Ala Ala Leu
                485                 490                 495

Ile Gln Ser Ala Arg Asp Leu Tyr Gly Ser Gln Asp Ala Ala Ser Val
            500                 505                 510

Glu Ala Ala Trp Asn Ala Val Gly Leu
            515                 520

<210> SEQ ID NO 2
<211> LENGTH: 274
<212> TYPE: PRT
<213> ORGANISM: Thermomyces lanuginosus

<400> SEQUENCE: 2

Glu Val Ser Gln Asp Leu Phe Asn Gln Phe Asn Leu Phe Ala Gln Tyr
1               5                   10                  15

Ser Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
            35                  40                  45

Ala Thr Phe Leu Tyr Ser Phe Glu Asp Ser Gly Val Gly Asp Val Thr
50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Ala Asn Leu Asn Phe Trp
                85                  90                  95

Leu Lys Lys Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gln Ala Thr Asp Ala Cys Asn Ala Gly Gly
            260                 265                 270

Phe Ser
```

```
<210> SEQ ID NO 3
<211> LENGTH: 291
<212> TYPE: PRT
<213> ORGANISM: Thermomyces lanuginosus

<400> SEQUENCE: 3

Met Arg Ser Ser Leu Val Leu Phe Phe Val Ser Ala Trp Thr Ala Leu
1               5                   10                  15

Ala Ser Pro Ile Arg Arg Glu Val Ser Gln Asp Leu Phe Asn Gln Phe
            20                  25                  30

Asn Leu Phe Ala Gln Tyr Ser Ala Ala Tyr Cys Gly Lys Asn Asn
        35                  40                  45

Asp Ala Pro Ala Gly Thr Asn Ile Thr Cys Thr Gly Asn Ala Cys Pro
50                  55                  60

Glu Val Glu Lys Ala Asp Ala Thr Phe Leu Tyr Ser Phe Glu Asp Ser
65                  70                  75                  80

Gly Val Gly Asp Val Thr Gly Phe Leu Ala Leu Asp Asn Thr Asn Lys
                85                  90                  95

Leu Ile Val Leu Ser Phe Arg Gly Ser Arg Ser Ile Glu Asn Trp Ile
            100                 105                 110

Gly Asn Leu Asn Phe Asp Leu Lys Glu Ile Asn Asp Ile Cys Ser Gly
        115                 120                 125

Cys Arg Gly His Asp Gly Phe Thr Ser Ser Trp Arg Ser Val Ala Asp
130                 135                 140

Thr Leu Arg Gln Lys Val Glu Asp Ala Val Arg Glu His Pro Asp Tyr
145                 150                 155                 160

Arg Val Val Phe Thr Gly His Ser Leu Gly Gly Ala Leu Ala Thr Val
                165                 170                 175

Ala Gly Ala Asp Leu Arg Gly Asn Gly Tyr Asp Ile Asp Val Phe Ser
            180                 185                 190

Tyr Gly Ala Pro Arg Val Gly Asn Arg Ala Phe Ala Glu Phe Leu Thr
        195                 200                 205

Val Gln Thr Gly Gly Thr Leu Tyr Arg Ile Thr His Thr Asn Asp Ile
210                 215                 220

Val Pro Arg Leu Pro Pro Arg Glu Phe Gly Tyr Ser His Ser Ser Pro
225                 230                 235                 240

Glu Tyr Trp Ile Lys Ser Gly Thr Leu Val Pro Val Arg Arg Arg Asp
                245                 250                 255

Ile Val Lys Ile Glu Gly Ile Asp Ala Thr Gly Gly Asn Asn Gln Pro
            260                 265                 270

Asn Ile Pro Asp Ile Pro Ala His Leu Trp Tyr Phe Gly Leu Ile Gly
        275                 280                 285

Thr Cys Leu
    290

<210> SEQ ID NO 4
<211> LENGTH: 245
<212> TYPE: PRT
<213> ORGANISM: Aspergillus aculeatus

<400> SEQUENCE: 4

Val Pro Met Gly Ser Arg Thr Lys Asn Leu Ala Thr Arg Ala Thr Asn
1               5                   10                  15

Ala Val Val Ser Val Ser Ser Leu Ala Ala Thr Thr Leu Lys Asp Asn
            20                  25                  30

Asp Gly Ser Gly Ala Gly Gln Asp Val Tyr Thr Phe His Thr Gly Asp
```

```
                35                  40                  45
Gly Ser Val Ala Asp Gly Trp Pro Ala Gln Ser Ser Trp Val Ser Phe
 50                  55                  60

Asp Asp Met Trp Lys Ala Asn Lys Pro Thr Ile Met Glu Ser Cys Thr
 65                  70                  75                  80

Gln Phe Gly Val Pro Asn Asn Ser Ala Asn Glu Thr Gln Asn Leu Tyr
                 85                  90                  95

Asp Ala Ile Gln Gln Val Ala Lys Glu Ser His Leu Asp His Arg Phe
            100                 105                 110

Ile Leu Ala Ile Ile Met Gln Glu Ser Lys Gly Cys Val Arg Val His
        115                 120                 125

Thr Thr Asn Tyr Gly Val Arg Asn Pro Gly Leu Met Gln Asp His Asp
130                 135                 140

Gly Ala Gly Thr Cys Asn Asp Asn Gly Val Val Gln Asn Pro Cys Pro
145                 150                 155                 160

Lys Asn Glu Ile Leu Gln Met Val Arg Asp Gly Ala Ile Gly Thr Ala
                165                 170                 175

Ala Gly Asp Gly Leu Ala Ser Leu Ile Asp Gln Gln Gly Lys Thr Asp
            180                 185                 190

Val Ser Gly Phe Tyr Arg Ala Ala Arg Leu Tyr Asn Ser Gly Ser Ile
        195                 200                 205

Ser Asp Ala Ser Asn Leu Asn Val Gly Val Gly Thr Ala Cys Tyr Ala
210                 215                 220

Thr Asp Val Ala Asn Arg Leu Thr Gly Trp Val Asn Ala Ala Ser Lys
225                 230                 235                 240

Cys Thr Leu Ser Ala
                245

<210> SEQ ID NO 5
<211> LENGTH: 582
<212> TYPE: PRT
<213> ORGANISM: Rhizomucor pusillus

<400> SEQUENCE: 5

Ala Thr Ser Asp Asp Trp Lys Gly Lys Ala Ile Tyr Gln Leu Leu Thr
 1               5                  10                  15

Asp Arg Phe Gly Arg Ala Asp Asp Ser Thr Ser Asn Cys Ser Asn Leu
                20                  25                  30

Ser Asn Tyr Cys Gly Gly Thr Tyr Glu Gly Ile Thr Lys His Leu Asp
            35                  40                  45

Tyr Ile Ser Gly Met Gly Phe Asp Ala Ile Trp Ile Ser Pro Ile Pro
 50                  55                  60

Lys Asn Ser Asp Gly Gly Tyr His Gly Tyr Trp Ala Thr Asp Phe Tyr
 65                  70                  75                  80

Gln Leu Asn Ser Asn Phe Gly Asp Glu Ser Gln Leu Lys Ala Leu Ile
                 85                  90                  95

Gln Ala Ala His Glu Arg Asp Met Tyr Val Met Leu Asp Val Val Ala
            100                 105                 110

Asn His Ala Gly Pro Thr Ser Asn Gly Tyr Ser Gly Tyr Thr Phe Gly
        115                 120                 125

Asp Ala Ser Leu Tyr His Pro Lys Cys Thr Ile Asp Tyr Asn Asp Gln
130                 135                 140

Thr Ser Ile Glu Gln Cys Trp Val Ala Asp Glu Leu Pro Asp Ile Asp
145                 150                 155                 160
```

```
Thr Glu Asn Ser Asp Asn Val Ala Ile Leu Asn Asp Ile Val Ser Gly
                165                 170                 175
Trp Val Gly Asn Tyr Ser Phe Asp Gly Ile Arg Ile Asp Thr Val Lys
            180                 185                 190
His Ile Arg Lys Asp Phe Trp Thr Gly Tyr Ala Glu Ala Ala Gly Val
        195                 200                 205
Phe Ala Thr Gly Glu Val Phe Asn Gly Asp Pro Ala Tyr Val Gly Pro
    210                 215                 220
Tyr Gln Lys Tyr Leu Pro Ser Leu Ile Asn Tyr Pro Met Tyr Tyr Ala
225                 230                 235                 240
Leu Asn Asp Val Phe Val Ser Lys Ser Lys Gly Phe Ser Arg Ile Ser
                245                 250                 255
Glu Met Leu Gly Ser Asn Arg Asn Ala Phe Glu Asp Thr Ser Val Leu
            260                 265                 270
Thr Thr Phe Val Asp Asn His Asp Asn Pro Arg Phe Leu Asn Ser Gln
        275                 280                 285
Ser Asp Lys Ala Leu Phe Lys Asn Ala Leu Thr Tyr Val Leu Leu Gly
    290                 295                 300
Glu Gly Ile Pro Ile Val Tyr Tyr Gly Ser Glu Gln Gly Phe Ser Gly
305                 310                 315                 320
Gly Ala Asp Pro Ala Asn Arg Glu Val Leu Trp Thr Thr Asn Tyr Asp
                325                 330                 335
Thr Ser Ser Asp Leu Tyr Gln Phe Ile Lys Thr Val Asn Ser Val Arg
            340                 345                 350
Met Lys Ser Asn Lys Ala Val Tyr Met Asp Ile Tyr Val Gly Asp Asn
        355                 360                 365
Ala Tyr Ala Phe Lys His Gly Asp Ala Leu Val Val Leu Asn Asn Tyr
    370                 375                 380
Gly Ser Gly Ser Thr Asn Gln Val Ser Phe Ser Val Ser Gly Lys Phe
385                 390                 395                 400
Asp Ser Gly Ala Ser Leu Met Asp Ile Val Ser Asn Ile Thr Thr Thr
                405                 410                 415
Val Ser Ser Asp Gly Thr Val Thr Phe Asn Leu Lys Asp Gly Leu Pro
            420                 425                 430
Ala Ile Phe Thr Ser Ala Thr Gly Gly Thr Thr Thr Ala Thr Pro
    435                 440                 445
Thr Gly Ser Gly Ser Val Thr Ser Thr Ser Lys Thr Thr Ala Thr Ala
    450                 455                 460
Ser Lys Thr Ser Thr Ser Ser Thr Ser Cys Thr Thr Pro Thr Ala
465                 470                 475                 480
Val Ala Val Thr Phe Asp Leu Thr Ala Thr Thr Thr Tyr Gly Glu Asn
                485                 490                 495
Ile Tyr Leu Val Gly Ser Ile Ser Gln Leu Gly Asp Trp Glu Thr Ser
            500                 505                 510
Asp Gly Ile Ala Leu Ser Ala Asp Lys Tyr Thr Ser Ser Asp Pro Leu
        515                 520                 525
Trp Tyr Val Thr Val Thr Leu Pro Ala Gly Glu Ser Phe Glu Tyr Lys
    530                 535                 540
Phe Ile Arg Ile Glu Ser Asp Asp Ser Val Glu Trp Glu Ser Asp Pro
545                 550                 555                 560
Asn Arg Glu Tyr Thr Val Pro Gln Ala Cys Gly Thr Ser Thr Ala Thr
                565                 570                 575
Val Thr Asp Thr Trp Arg
```

```
                580

<210> SEQ ID NO 6
<211> LENGTH: 309
<212> TYPE: PRT
<213> ORGANISM: Bacillus bogoriensis

<400> SEQUENCE: 6

Ala Asn Ser Gly Phe Tyr Val Ser Gly Thr Thr Leu Tyr Asp Ala Asn
1               5                   10                  15

Gly Asn Pro Phe Val Met Arg Gly Ile Asn His Gly His Ala Trp Tyr
            20                  25                  30

Lys Asp Gln Ala Thr Thr Ala Ile Glu Gly Ile Ala Asn Thr Gly Ala
        35                  40                  45

Asn Thr Val Arg Ile Val Leu Ser Asp Gly Gln Trp Thr Lys Asp
    50                  55                  60

Asp Ile His Thr Val Arg Asn Leu Ile Ser Leu Ala Glu Asp Asn His
65                  70                  75                  80

Leu Val Ala Val Leu Glu Val His Asp Ala Thr Gly Tyr Asp Ser Ile
                85                  90                  95

Ala Ser Leu Asn Arg Ala Val Asp Tyr Trp Ile Glu Met Arg Ser Ala
            100                 105                 110

Leu Ile Gly Lys Glu Asp Thr Val Ile Ile Asn Ile Ala Asn Glu Trp
        115                 120                 125

Phe Gly Ser Trp Glu Gly Asp Ala Trp Ala Asp Gly Tyr Lys Gln Ala
130                 135                 140

Ile Pro Arg Leu Arg Asn Ala Gly Leu Asn His Thr Leu Met Val Asp
145                 150                 155                 160

Ala Ala Gly Trp Gly Gln Phe Pro Gln Ser Ile His Asp Tyr Gly Arg
                165                 170                 175

Glu Val Phe Asn Ala Asp Pro Gln Arg Asn Thr Met Phe Ser Ile His
            180                 185                 190

Met Tyr Glu Tyr Ala Gly Gly Asn Ala Ser Gln Val Arg Thr Asn Ile
        195                 200                 205

Asp Arg Val Leu Asn Gln Asp Leu Ala Leu Val Ile Gly Glu Phe Gly
    210                 215                 220

His Arg His Thr Asn Gly Asp Val Asp Glu Ala Thr Ile Met Ser Tyr
225                 230                 235                 240

Ser Glu Gln Arg Gly Val Gly Trp Leu Ala Trp Ser Trp Lys Gly Asn
                245                 250                 255

Gly Pro Glu Trp Glu Tyr Leu Asp Leu Ser Asn Asp Trp Ala Gly Asn
            260                 265                 270

Asn Leu Thr Ala Trp Gly Asn Thr Ile Val Asn Gly Pro Tyr Gly Leu
        275                 280                 285

Arg Glu Thr Ser Arg Leu Ser Thr Val Phe Thr Gly Gly Gly Ser Asp
    290                 295                 300

Gly Gly Thr Ser Pro
305
```

SOLUBILIZATION OF MSW WITH BLEND ENZYMES

CROSS-REFERENCE TO RELATED APPLICATIONS

This application is a national stage filing under 35 U.S.C. 371 of PCT/EP2015/069685 filed Aug. 27, 2015, which International Application was published by the International Bureau in English on Mar. 3, 2016, and application claims priority from European Patent Application No. 14182698.2, filed Aug. 28, 2014, which applications are hereby incorporated in their entirety by reference in this application.

REFERENCE TO SEQUENCE LISTING

This application contains a Sequence Listing in computer readable form. The computer readable form is incorporated herein by reference.

FIELD OF THE INVENTION

The present invention relates to a method for solubilisation or hydrolysis of Municipal Solid Waste (MSW) with an enzyme blend, optionally for subsequent production of biogas and/or bioethanol.

BACKGROUND OF THE INVENTION

Municipal Solid Waste (MSW) is commonly also known as trash, garbage, refuse or rubbish. It consists of solid waste fractions that typically comes from municipalities and includes for instance waste from homes, schools, offices, hospitals, institutions etc. MSW is produced world-wide in very large quantities; thus in EU alone 2.44 million tons were generated in 2012 (Eurostat, 2014). The challenges of MSW production are many and may include collection, sorting, treatment, and disposal. Furthermore, well known environmental issues such as air and groundwater pollution from landfills is related to MSW. With an increasing world population entailing an increasing waste production, proper sustainable MSW management is a global challenge.

Although being environmental troublesome MSW also represents a large unexploited resource that may be used for energy production and recycling/recovery of scarce resources. Incineration is a technology that is widely used in some European countries, for instance Denmark, Sweden and Germany. The generation of energy is highly efficient but recovery of materials is limited. Furthermore, incineration of MSW results in a large production of slag (ash) which for some types of waste fractions can have environmental negative impacts (Idris and Saed 2002, Journal of Hazardous Materials B93 201-208). Capture of gas generated from anaerobic digestion of organic material at landfills is another way of generating energy from MSW but this technology also has a very low efficiency in materials recycling.

Integrated processes with concurrent energy production and recycling of materials are an attractive solution that has become a lot of attention lately. In such waste refineries, organic parts of MSW represent a resource that potentially can be used for bioenergy production in the form of for instance biogas (Hartmann and Ahring, 2006, Water Science & Technology Vol 53 No 8 p. 7-22). However, sorting of MSW in organic fractions for bioenergy production and plastic/metal fractions for material recovery is not easy due to the very inhomogeneous nature of MSW. As described by Jensen et al. (2012) (WO 2013/185777) presorting of MSW is typically costly, inefficient or impractical while source-sorting requires large infrastructure and operating expenses as well as active participation from the community from which the waste is collected.

Enzymatic treatment of MSW has lately been described and seems like a very interesting and innovative approach in the MSW management (Jensen et al. 2010, Waste Management 30, p. 2497-2503; Jensen et al. 2011, Biochem Biotechnol 165, p. 1799-1811; Tonini and Astrup 2012, Waste Management 32, p. 165-176). This technology is based on a liquefaction/solubilization step of organic degradable parts with hydrolytic enzymes and a subsequent separation of the MSW into a bioliquid and solids. The bioliquid can be used for biogas production while the solids can be further sorted and used for recycling or combusted according to the composition of the material. The technology has proven very robust at even high dry matter concentrations (35%) and has been demonstrated in pilot/demonstration facilities treating up to 1 ton of MSW/hour.

Tonini and Astrup (2012), evaluated the environmental sustainability—using life-cycle assessment—of four different waste refinery scenarios using this enzymatic liquefaction technology. Their assessment was based on a pilot-scale facility established at a Danish incinerator Amagerforbrænding in Copenhagen, Denmark. The different scenarios were compared to incineration. The authors concluded that "enzymatic refining of the waste with utilization of the products for energy recovery can represent a valuable alternative to incineration from both an energy and environmental point of view. This is the case if the downstream energy options for exploiting the solid and liquid fractions are co-combustion and anaerobic digestion for biogas production". The authors also concluded that cost savings of the waste refinery was related to a higher recovery of metals and energy. Furthermore, "improvement in the environmental as well as energy performance of the waste refinery itself was primarily related to the optimization of energy and enzymes consumption".

The use of cellulases (for instance Novozymes A/S Celluclast® 1.5 L, Novozymes A/S CELLIC® Ctec2 and Novozymes A/S CELLIC® Ctec3) for liquefaction of MSW with subsequent separation of unsorted waste into a bioliquid—used for biogas production—and into inorganic valuable products suitable for recycling has been clearly illustrated (WO2013/185777A1, the content of which is hereby incorporated by reference). However, with MSW being a complex substrate containing other organic components than cellulose (e.g. protein and lipids) it seems reasonable that the liquefaction process can be further improved by supplementing cellulases with other enzyme activities. Until now this theory has not been proven. An attempt was made Jensen et al. 2010 who tested a protease (Novozymes A/S Alcalase 2.5 L) and a α-amylase (Novozymes A/S Liquozyme® SC DC) as single enzymes and in combination with a cellulase (Novozymes A/S Celluclast® 1.5 L). "The cellulytic enzyme was the key catalyst in the liquefaction of degradable fractions both in terms of lowering viscosity and particle size distribution". No effect of the α-amylase and protease and interaction in between and with the cellulase was found. Nevertheless, it would be beneficial to provide an enzymes mix with a higher efficiency for liquefying MSW than the cellulases previously tested (Celluclast® 1.5 L, CELLIC® Ctec2 and CELLIC® Ctec3). Such invention could contribute to a global change in MSW management practices and turn an environmental problem into a profitable and environmentally beneficial solution.

SUMMARY OF THE INVENTION

The present invention relates to an enzyme composition for solubilization of Municipal Solid Waste (MSW), the enzyme composition comprising a cellulolytic background composition (CBC), and one or more enzymes selected from (i) a protease; (ii) a lipase and (iii) a beta-glucanase. In one embodiment, the composition further comprises one or more enzymes selected from (iv) a pectate lyase; (v) a mannanase and (vi) an amylase.

In one embodiment of the invention, the cellulolytic background composition (CBC) comprises one or more enzymes selected from a) a cellobiohydrolase I or variant thereof; (b) cellobiohydrolase II or variant thereof; (c) beta-glucosidase or variant thereof; and (d) a polypeptide having cellulolytic enhancing activity; or homologs thereof. In a further embodiment of the invention the cellulolytic background composition comprise one or more enzymes selected from (a) an *Aspergillus fumigatus* cellobiohydrolase I or variant thereof; (b) an *Aspergillus fumigatus* cellobiohydrolase II or variant thereof; (c) an *Aspergillus fumigatus* beta-glucosidase or variant thereof; and (d) a *Penicillium* sp. GH61 polypeptide having cellulolytic enhancing activity; or homologs thereof.

In a related embodiment of the invention the (i) a protease is derived from the genus *Bacillus*, such as e.g. *Bacillus amyloliquefaciens* such as e.g. the protease encoded by SEQ ID NO: 1, or a protease having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 1.

In a related embodiment of the invention the (ii) a lipase is derived from the genus *Thermomyces* sp. such as e.g. *Thermomyces lanuginosus* such as e.g. the lipase encoded by SEQ ID NO: 2 (or a lipase having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 2) or wherein the (ii) a lipase is derived from the genus *Humicola* sp. such as e.g. *Humicola insolens* (or a lipase having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the *Humicola insolens* lipase). In a related embodiment of the invention the (iii) a beta-glucanase is derived from a member of the genus *Aspergillus* such as e.g. *Aspergillus aculeatus* such as e.g. the beta-glucanase encoded by the sequence encoded by SEQ ID NO: 4 or homologs thereof (e.g., a beta-glucanase having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 4). In a related embodiment of the invention the (iv) a pectate lyase forms part of a multicomponent enzyme composition comprising pectate lyase, xylanase and cellulase activities such as e.g. Novozym 81243™. In a related embodiment of the invention the (v) a mannanase is an endo-mannosidase derived from the genus *Bacillus* such as e.g. *Bacillus bogoriensis* such as e.g. the endo-mannosidase encoded by SEQ ID NO: 6 or homologs thereof (e.g., an endo-mannosidase having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 6). In a related embodiment of the invention the (vi) an amylase is an alpha-amylase derived from the genus *Rhozimucor* such as e.g. *Rhizomucor pusillus* such as e.g. the alpha-amylase encoded by SEQ ID NO: 5 or homologs thereof (e.g., an alpha-amylase having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 5).

In yet a related embodiment, the protease is present at a ratio between 0-20% w/w, such as e.g. 10% w/w of the total enzyme protein. In a related embodiment of the invention the the beta-glucanase is present at a ratio between 0-30% w/w, such as e.g. 15% w/w of the total enzyme protein. In a yet another related embodiment of the invention the pectate-lyase is present at a ratio between 0-10% w/w, such as e.g. 5% w/w of the total enzyme protein. In a yet another related embodiment of the invention the mannanase or amylase is present at a ratio between 0-10% w/w, such as e.g. 5% w/w of the total enzyme protein. In a yet another related embodiment of the invention the cellulolytic enzyme blend is present at a ratio between 40%-99% w/w, such as e.g. between 50%-90% w/w, such as e.g. 60%-80% w/w, such as e.g. 65-75% of the total enzyme protein. In a yet another related embodiment of the invention the enzyme composition further comprises one or more enzymes selected from a cellulase, an AA9 polypeptide, a hemicellulase, a cellulose inducible protein (CIP) an esterase, an expansin, a ligninolytic enzyme, an oxidoreductase, a pectinase, a protease, and a swollenin. In a yet another related embodiment of the invention the hemicellulase is one or more enzymes selected from the group consisting of a xylanase, an acetylxylan esterase, a feruloyl esterase, an arabinofuranosidase, a xylosidase, and a glucuronidase.

A related aspect of present invention relates to a process for solubilizing waste comprising: contacting waste with the enzyme composition of the invention, wherein the waste may be Municipal Solid Waste (MSW).

Yet a related aspect of the invention relates to a process for producing a fermentation product, comprising: (a) treating MSW with the enzyme composition of the present invention, (b) fermenting the solubilized and/or hydrolysed MSW with one or more fermenting microorganisms to produce a fermentation product; and, (c) recovering the fermentation product from the fermentation. The waste in said process may be pretreated.

We have tested a variety of commercial enzymes on a model-substrate of MSW and used dry matter solubilisation of the substrate as a parameter for the liquefaction effect of the enzymes. The model waste simulated the organic fractions of MSW (based on a publication of the composition of Danish MSW; Riber et al. 2009, Waste Management 29, p. 1251-1257), and consisted of a vegetable fraction (eg. Carrots, potatoes, cereals etc.) animal by-product fraction (e.g. cheese and meats) and cellulose fraction (e.g. paper, card-board, textile).

The screening experiments were carried out in 20 gram scale at 50° C. for 24 hours. Some specific enzymes improved the dry matter solubilisation of the model waste when they replaced parts of the Cellulolytic Background Composition (CBC), including some proteases, lipases and beta-glucanases. Subsequently, candidates were selected for further testing in blending experiments.

The invention provides a process for solubilizing MSW by adding one or more enzymes—including acid protease, acid lipase and acid beta-glucanase—in combination with a cellulase composition at a suitable temperature and pH to MSW.

As apparent from the findings disclosed herein, it was surprisingly found that a synergistic effect in solubilization of the MSW was obtained when adding blends of different enzymes to a cellulolytic background composition (27.1%), compared to the individual contributions of e.g. components B.a protease, T.l pholip and A.a BG which was up to 5%, 8.5% and 8.2% respectively.

BRIEF DESCRIPTION OF DRAWINGS

FIG. 5 shows a data table from dose response experiments with blend enzymes and CBC and model waste. The table illustrates the amount of glucose, xylose and lactic acid at different enzyme concentrations.

DEFINITIONS

Figure 1:
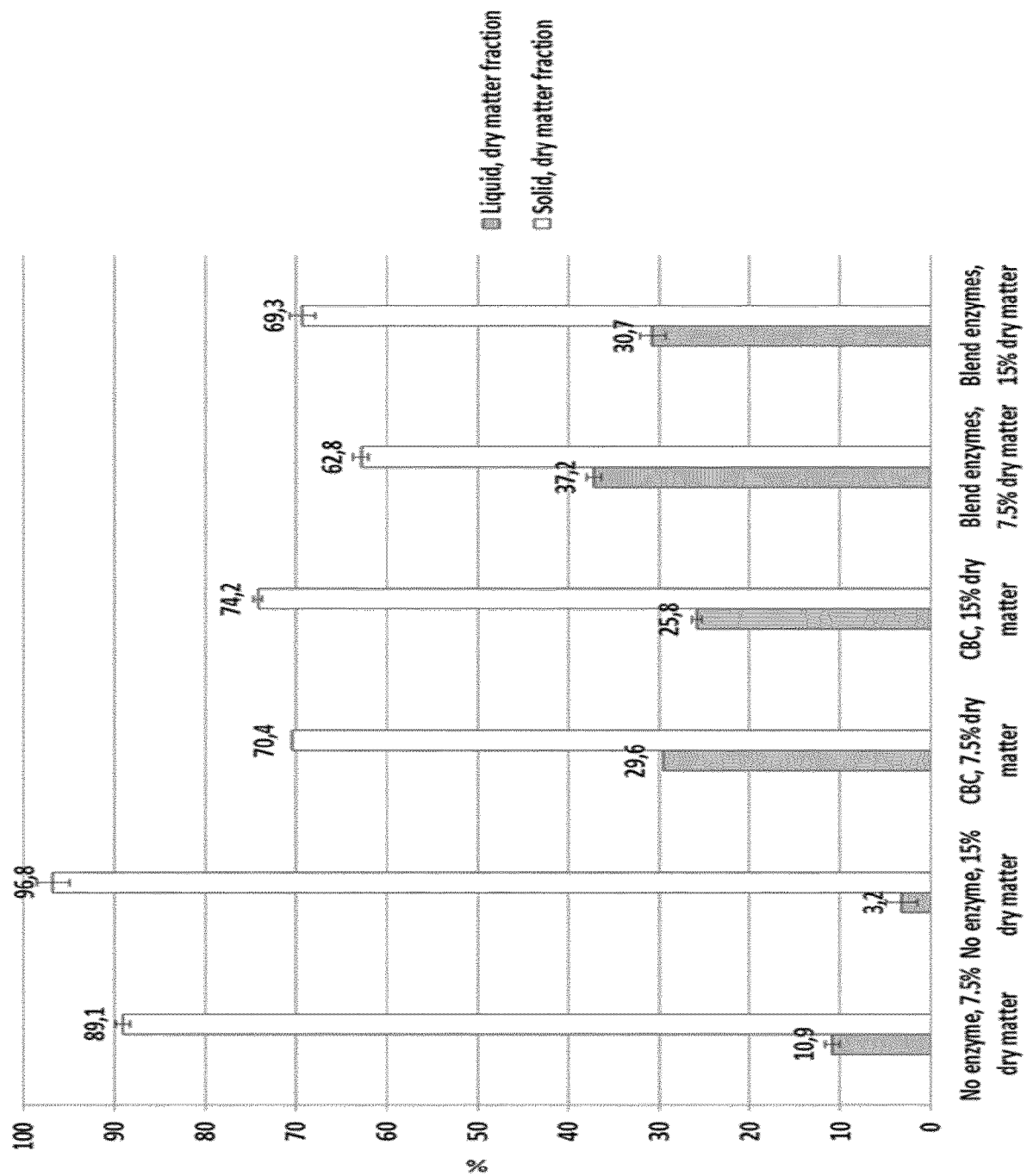
FIG. 1 shows solubilization of model waste in free fall experiments at two different dry matter concentrations. The figure shows the distribution of dry matter liquid (grey bars) and solids fractions (white bars).

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. Acetylxylan esterase activity can be determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans.

Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. Alpha-L-arabinofuranosidase activity can be determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. Alpha-glucuronidase activity can be determined according to de Vries, 1998, *J. Bacteriol.* 180: 243-249. One unit of alpha-glucuronidase equals the amount of enzyme capable of releasing 1 μmole of glucuronic or 4-O-methylglucuronic acid per minute at pH 5, 40° C.

Auxiliary Activity 9 polypeptide: The term "Auxiliary Activity 9 polypeptide" or "AA9 polypeptide" means a polypeptide classified as a lytic polysaccharide monooxygenase (Quinlan et al., 2011, *Proc. Natl. Acad. Sci. USA* 208: 15079-15084; Phillips et al., 2011, *ACS Chem.* Biol. 6: 1399-1406; Lin et al., 2012, *Structure* 20: 1051-1061). AA9 polypeptides were formerly classified into the glycoside hydrolase Family 61 (GH61) according to Henrissat, 1991, *Biochem. J.* 280: 309-316, and Henrissat and Bairoch, 1996, *Biochem. J.* 316: 695-696.

AA9 polypeptides enhance the hydrolysis of a cellulosic material by an enzyme having cellulolytic activity. Cellulolytic enhancing activity can be determined by measuring the increase in reducing sugars or the increase of the total of cellobiose and glucose from the hydrolysis of a cellulosic material by cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of an AA9 polypeptide for 1-7 days at a suitable temperature, such as 40° C.-80° C., e.g., 40° C., 45° C., 50° C., 55° C., 60° C., 65° C., 70° C., 75° C., or 80° C. and a suitable pH, such as 4-9, e.g., 4.5, 5.0, 5.5, 6.0, 6.5, 7.0, 7.5, 8.0, 8.5, or 9.0, compared to a control hydrolysis with equal total protein loading without cellulolytic enhancing activity (1-50 mg of cellulolytic protein/g of cellulose in PCS).

AA9 polypeptide enhancing activity can be determined using a mixture of CELLUCLAST® 1.5 L (Novozymes A/S, Bagsværd, Denmark) and beta-glucosidase as the source of the cellulolytic activity, wherein the beta-glucosidase is present at a weight of at least 2-5% protein of the cellulase protein loading. In one aspect, the beta-glucosidase is an *Aspergillus oryzae* beta-glucosidase (e.g., recombinantly produced in *Aspergillus oryzae* according to WO 02/095014). In another aspect, the beta-glucosidase is an *Aspergillus fumigatus* beta-glucosidase (e.g., recombinantly produced in *Aspergillus oryzae* as described in WO 02/095014).

AA9 polypeptide enhancing activity can also be determined by incubating an AA9 polypeptide with 0.5% phosphoric acid swollen cellulose (PASC), 100 mM sodium acetate pH 5, 1 mM MnSO$_4$, 0.1% gallic acid, 0.025 mg/ml of *Aspergillus fumigatus* beta-glucosidase, and 0.01% TRITON® X-100 (4-(1,1,3,3-tetramethylbutyl)phenyl-polyethylene glycol) for 24-96 hours at 40° C. followed by determination of the glucose released from the PASC.

AA9 polypeptide enhancing activity can also be determined according to WO 2013/028928 for high temperature compositions.

AA9 polypeptides enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

The AA9 polypeptide can also be used in the presence of a soluble activating divalent metal cation according to WO 2008/151043 or WO 2012/122518, e.g., manganese or copper.

The AA9 polypeptide can be used in the presence of a dioxy compound, a bicylic compound, a heterocyclic compound, a nitrogen-containing compound, a quinone compound, a sulfur-containing compound, or a liquor obtained from a pretreated cellulosic or hemicellulosic material such as pretreated corn stover (WO 2012/021394, WO 2012/021395, WO 2012/021396, WO 2012/021399, WO 2012/021400, WO 2012/021401, WO 2012/021408, and WO 2012/021410).

Beta-glucanase: The term "beta-glucanase" means any type of endo-beta-glucanase that hydrolyzes (1,3)- or (1,4)-linkages in beta-D-glucans (E.C. 3.2.1.73) (E.C.3.2.1.6).

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. Beta-glucosidase activity can be determined using p-nitrophenyl-beta-D-glucopyranoside as substrate according to the procedure of Venturi et al., 2002, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. Beta-xylosidase activity can be determined using 1 mM p-nitrophenyl-beta-D-xyloside as substrate in 100 mM sodium citrate containing 0.01% TWEEN® 20 at pH 5, 40° C. One unit of beta-xylosidase is defined as 1.0 μmole of p-nitrophenolate anion produced per minute at 40° C., pH 5 from 1 mM p-nitrophenyl-beta-D-xyloside in 100 mM sodium citrate containing 0.01% TWEEN® 20.

Binding domain: The term "binding domain" e.g., "cellulose binding domain" means the region of an enzyme that mediates binding of the enzyme to amorphous regions of a cellulose substrate. The cellulose binding domain (CBD) is typically found either at the N-terminal or at the C-terminal extremity of an enzyme.

Catalytic domain: The term "catalytic domain" means the region of an enzyme containing the catalytic machinery of the enzyme.

Carbohydrate binding module: The term "carbohydrate binding module" means a domain within a carbohydrate-active enzyme that provides carbohydrate-binding activity (Boraston et al., 2004, *Biochem. J.* 383: 769-781). A majority of known carbohydrate binding modules (CBMs) are contiguous amino acid sequences with a discrete fold. The carbohydrate binding module (CBM) is typically found either at the N-terminal or at the C-terminal extremity of an enzyme. Some CBMs are known to have specificity for cellulose.

Catalase: The term "catalase" means a hydrogen-peroxide:hydrogen-peroxide oxidoreductase (EC 1.11.1.6) that catalyzes the conversion of $2H_2O_2$ to $O_2 + 2 H_2O$. For purposes of the present invention, catalase activity is determined according to U.S. Pat. No. 5,646,025. One unit of catalase activity equals the amount of enzyme that catalyzes the oxidation of 1 μmole of hydrogen peroxide under the assay conditions.

Catalytic domain: The term "catalytic domain" means the region of an enzyme containing the catalytic machinery of the enzyme.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, *Trends in Biotechnology* 15: 160-167; Teeri et al., 1998, *Biochem. Soc. Trans.* 26: 173-178). Cellobiohydrolase activity can be determined according to the procedures described by Lever et al., 1972, *Anal. Biochem.* 47: 273-279; van Tilbeurgh et al., 1982, *FEBS Letters* 149: 152-156; van Tilbeurgh and Claeyssens, 1985, *FEBS Letters* 187: 283-288; and Tomme et al., 1988, *Eur. J. Biochem.* 170: 575-581.

Cellulolytic Background Composition (CBC) or Cellulolytic Enzyme Blend:

The term "Cellulolytic background composition" or "CBC" means an enzyme composition comprising a mixture of two or more cellulolytic enzymes. In one embodiment the CBC comprises two or more cellulolytic enzymes selected from: i) an *Aspergillus fumigatus* cellobiohydrolase I; (ii) an *Aspergillus fumigatus* cellobiohydrolase II; (iii) an *Aspergillus fumigatus* beta-glucosidase or variant thereof; and (iv) a *Penicillium* sp. GH61 polypeptide having cellulolytic enhancing activity; or homologs thereof. The CBC may further comprise one or more enzymes selected from: (a) an *Aspergillus fumigatus* xylanase or homolog thereof, (b) an *Aspergillus fumigatus* beta-xylosidase or homolog thereof; or (c) a combination of (a) and (b) (as described in further detail in WO 2013/028928). The CBC may be any CBC described in WO 2013/028928 (the content of which is hereby incorporated by reference). In one embodiment, the CBC is CELLIC® Ctec3 obtainable from Novozymes A/S (Bagsværd, Denmark).

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, *Biotechnology Advances* 24: 452-481. Total cellulolytic enzyme activity can be measured using insoluble substrates, including Whatman N°1 filter paper, microcrystalline cellulose, bacterial cellulose, algal cellulose, cotton, pretreated lignocellulose, etc. The most common total cellulolytic activity assay is the filter paper assay using Whatman N°1 filter paper as the substrate. The assay was established by the International Union of Pure and Applied Chemistry (IUPAC) (chose, 1987, *Pure Appl. Chem.* 59: 257-68).

Cellulolytic enzyme activity can be determined by measuring the increase in production/release of sugars during hydrolysis of a cellulosic material by cellulolytic enzyme(s) under the following conditions: 1-50 mg of cellulolytic enzyme protein/g of cellulose in pretreated corn stover (PCS) (or other pretreated cellulosic material) for 3-7 days at a suitable temperature such as 40° C.-80° C., e.g., 40° C., 45° C., 50° C., 55° C., 60° C., 65° C., 70° C., 75° C., or 80° C., and a suitable pH, such as 4-9, e.g., 4.0, 4.5, 5.0, 5.5, 6.0, 6.5, 7.0, 7.5, 8.0, 8.5, or 9.0, compared to a control hydrolysis without addition of cellulolytic enzyme protein. Typical conditions are 1 ml reactions, washed or unwashed PCS, 5% insoluble solids (dry weight), 50 mM sodium acetate pH 5, 1 mM $MnSO_4$, 50° C., 55° C., or 60° C., 72 hours, sugar analysis by AMINEX® HPX-87H column chromatography (Bio-Rad Laboratories, Inc., Hercules, Calif., USA).

Cellulosic material: The term "cellulosic material" means any material containing cellulose.

In an embodiment, the cellulosic material is agricultural residue, herbaceous material (including energy crops), municipal solid waste, pulp and paper mill residue, waste paper, or wood (including forestry residue).

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Dissolved Oxygen Saturation Level: The saturation level of oxygen is determined at the standard partial pressure (0.21 atmosphere) of oxygen. The saturation level at the standard partial pressure of oxygen is dependent on the temperature and solute concentrations. In an embodiment where the temperature during hydrolysis is 50° C., the saturation level would typically be in the range of 5-5.5 mg oxygen per kg slurry, depending on the solute concentrations. Hence, a concentration of dissolved oxygen of 0.5 to 10% of the saturation level at 50° C. corresponds to an amount of dissolved oxygen in a range from 0.025 ppm (0.5×5/100) to 0.55 ppm (10×5.5/100), such as, e.g., 0.05 to 0.165 ppm, and a concentration of dissolved oxygen of 10-70% of the saturation level at 50° C. corresponds to an amount of dissolved oxygen in a range from 0.50 ppm (10×5/100) to 3.85 ppm (70×5.5/100), such as, e.g., 1 to 2 ppm. In an embodiment, oxygen is added in an amount in the range of 0.5 to 5 ppm, such as 0.5 to 4.5 ppm, 0.5 to 4 ppm, 0.5 to 3.5 ppm, 0.5 to 3 ppm, 0.5 to 2.5 ppm, or 0.5 to 2 ppm.

Endoglucanase: The term "endoglucanase" means a 4-(1, 3; 1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3-1,4 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). Endoglucanase activity can also be determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase (FAE) is also known as ferulic acid esterase, hydroxycinnamoyl esterase, FAE-III, cinnamoyl ester hydrolase, FAEA, cinnAE, FAE-I, or FAE-II. Feruloyl esterase activity can be determined using 0.5 mM p-nitrophenylferulate as substrate in 50 mM sodium acetate pH 5.0. One unit of feruloyl esterase equals the amount of enzyme capable of releasing 1 µmole of p-nitrophenolate anion per minute at pH 5, 25° C.

Fragment: The term "fragment" means a polypeptide or a catalytic or binding domain having one or more (e.g., several) amino acids absent from the amino and/or carboxyl terminus of a mature polypeptide or domain; wherein the fragment has enzymatic or substrate binding activity.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, 2003, *Current Opinion In Microbiology* 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature such as 40° C.-80° C., e.g., 40° C., 45° C., 50° C., 55° C., 60° C., 65° C., 70° C., 75° C., or 80° C., and a suitable pH such as 4-9, e.g., 4.0, 4.5, 5.0, 5.5, 6.0, 6.5, 7.0, 7.5, 8.0, 8.5, or 9.0.

Hemicellulosic material: The term "hemicellulosic material" means any material comprising hemicelluloses.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Lipase: The term "lipase" means any enzyme that catalyzes the hydrolysis of lipids and/or having hydrolytic activity in class EC 3.1.1.—as defined by Enzyme Nomenclature. Particular useful is triacyl glycerol lipases (E.C.3.1.1.3) and phospholipase A1 (EC 3.1.1.32) and phospholipase A2 (E.C.3.1.1.4), but also other phospholipases (E.C.3.1.1.5), (E.C.3.1.4.4), (E.C.3.1.4.11), (E.C.3.1.4.50), (E.C.3.1.4.54).

Mannanases: In the context of the present invention a "mannanase" is a beta-mannanase and defined as an enzyme belonging to EC 3.2.1.78 or E.C.3.2.1.25. Mannanases have been identified in several *Bacillus* organisms. For example, Talbot et al., *Appl. Environ. Microbiol.*, Vol. 56, No. 11, pp. 3505-3510 (1990) describes a beta-mannanase derived from *Bacillus stearothermophilus* having an optimum pH of 5.5-7.5. Mendoza et al., World J. Microbiol. Biotech., Vol. 10, No. 5, pp. 551-555 (1994) describes a beta-mannanase derived from *Bacillus subtilis* having an optimum activity at pH 5.0 and 55° C. JP-03047076 discloses a beta-mannanase derived from *Bacillus* sp., having an optimum pH of 8-10. JP-63056289 describes the production of an alkaline, thermostable beta-mannanase. JP-08051975 discloses alkaline beta-mannanases from alkalophilic *Bacillus* sp. AM-001. A purified mannanase from *Bacillus amyloliquefaciens* is disclosed in WO 97/11164. WO 94/25576 discloses an enzyme from *Aspergillus aculeatus*, CBS 101.43, exhibiting mannanase activity and WO 93/24622 discloses a mannanase isolated from *Trichoderma reesei*.

Mature polypeptide: The term "mature polypeptide" means a polypeptide in its final form following translation and any post-translational modifications, such as N-terminal processing, C-terminal truncation, glycosylation, phosphorylation, etc.

Mature polypeptide coding sequence: The term "mature polypeptide coding sequence" means a polynucleotide that encodes a mature polypeptide having enzymatic activity.

Municipal Solid Waste (MSW): The term "municipal solid waste" or "MSW" is intended to mean solid waste fractions that is typically available in municipalities (cities, towns, villages). MSW can be a combination of plant materials (fruit, vegetables, grains, corn etc), animal materials (meats etc.), cellulosic material (paper, cardboard, diapers, textile etc.), glass, plastic, metal. MSW includes the following but is not limited to any one or more of the following:

waste collected from homes, schools, hospitals, offices, business, industries such as restaurants and food processing industries. MSW can potentially have been treated by shredding or pulping devices.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Pretreated municipal solid waste material: The term "pretreated municipal solid waste material" means a municipal solid waste material derived from biomass by treatment with heat and dilute sulfuric acid, alkaline pretreatment, neutral pretreatment, or any pretreatment known in the art.

Protease: The term "protease" means any protease or proteolytic enzyme suitable for use under neutral or acidic conditions. Suitable proteases include those of animal, vegetable or microbial origin. Chemically or genetically modified mutants are included. Suitable proteases includes metallo endoprotease that hydrolyzes internal peptide bonds (E.C. 3.4.24.28), serine endoprotease that hydrolyzes internal peptide bonds (E.C:3.4.23.23), endoprotease that hydrolyzes peptide bonds at the carboxy side of lysine and arginine residues E.C.3.4.21.4), aminopeptidase (E.C. 3.4.11.1) and exopeptidase that liberates amino acids by hydrolysis of the N-terminal peptide bond (E.C. 3.4.11.1).

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

Solubilization: The term "solubilization" means enzymatic treatment of a substrate. In present disclosure, the terms "hydrolyzation", "liquefaction", "saccharification" and "solubilization" may be used interchangeably.

Variant: The term "variant" means a polypeptide comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, 2006, *Journal of the Science of Food and Agriculture* 86(11): 1636-1647; Spanikova and Biely, 2006, *FEBS Letters* 580(19): 4597-4601; Herrimann et al., 1997, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. A common total xylanolytic activity assay is based on production of reducing sugars from polymeric 4-O-methyl glucuronoxylan as described in Bailey et al., 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

Xylan degrading activity can be determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, *Anal. Biochem.* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. Xylanase activity can be determined with 0.2% AZCL-arabinoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

Reference to "about" a value or parameter herein includes aspects that are directed to that value or parameter per se. For example, description referring to "about X" includes the aspect "X".

As used herein and in the appended claims, the singular forms "a," "or," and "the" include plural referents unless the context clearly dictates otherwise. It is understood that the aspects of the invention described herein include "consisting" and/or "consisting essentially of" aspects.

Unless defined otherwise or clearly indicated by context, all technical and scientific terms used herein have the same meaning as commonly understood by one of ordinary skill in the art to which this invention belongs.

DETAILED DESCRIPTION OF THE INVENTION

In some embodiments of the invention enzymatic solubilization of MSW is carried out together with natural occurring microorganisms found in the waste (concurrent enzymatic and microbial hydrolysis and fermentation) or found in recycled process wastes/solutions.

In some embodiments the microbial growth has a pH lowering effect especially when metabolites like caboxylic acids and fatty acids (e.g. acetate, propionate, butyrate, lactate) is produced.

In other embodiments of the invention it might be an advantage to inoculate MSW using different microbial species. These might include microorganisms that shows extracellular cellulase activities, microorganisms capable of degrading lignin, acetate-producing microorganisms, propionate-producing microorganisms, butyrate-producing organisms, ethanol-producing microorganisms and lactate producing microorganisms. Such embodiments are further described in DONG patent page 21-25 (WO2013/185777, the content of which is hereby incorporated by reference)

In practicing embodiments of the invention it can be advantageous to adjust temperature and water and dry matter content of the MSW. Enzymes normally show an optimal temperature and dry matter range. Hydrolysis of MSW is normally performed with agitation. This can be in reactors providing agitation by free fall mixing (as also described by DONG WO2006/056838 and WO2011/032557), stirred-tank reactors or similar systems. Suitable process time, temperature and pH conditions can readily be determined by one skilled in the art and is dependent on MSW composition, dry matter concentration and enzyme.

The present invention is also directed to processes for using the compositions thereof.

The present invention also relates to processes for degrading a municipal solid waste material, comprising: treating the municipal solid waste material with an enzyme composition comprising a cellulolytic background composition combined with one or more enzymes selected from (i) a protease; (ii) a lipase and (iii) a beta-glucanase; and optionally combined with one or more further enzymes selected from (iv) a pectate lyase; (v) a mannanase and (vi) an amylase. In one aspect, the processes further comprise recovering the degraded municipal solid waste material. Soluble products of degradation of the municipal solid waste material can be separated from insoluble municipal solid waste material using a method known in the art such as, for example, centrifugation, filtration, or gravity settling. In preferred embodiments solubilized compounds can be converted to Biogas (mainly comprising $CH_4$ and $CO_2$) by anaerobic digestion. In other embodiments solubilized sugars can be converted to ethanol by fermentation.

The present invention also relates to processes of producing a fermentation product, comprising: (a) solubilizing a municipal solid waste material with an enzyme composition comprising a cellulolytic background composition combined with one or more enzymes selected from (i) a protease; (ii) a lipase and (iii) a beta-glucanase; and optionally combined with one or more further enzymes selected from (iv) a pectate lyase; (v) a mannanase and (vi) an amylase; (b) fermenting the solubilized municipal solid waste material with one or more (e.g., several) fermenting microorganisms to produce the fermentation product; and (c) recovering the fermentation product from the fermentation. In preferred embodiments solubilized compounds can be converted to biogas (mainly comprising $CH_4$ and $CO_2$) by anaerobic digestion. In other embodiments solubilized sugars can be converted to ethanol by fermentation.

The present invention also relates to processes of fermenting a municipal solid waste material, comprising: fermenting the municipal solid waste material with one or more (e.g., several) fermenting microorganisms, wherein the municipal solid waste material is saccharified with an enzyme composition comprising a cellulolytic background composition combined with one or more enzymes selected from (i) a protease; (ii) a lipase and (iii) a beta-glucanase; and optionally combined with one or more further enzymes selected from (iv) a pectate lyase; (v) a mannanase and (vi) an amylase. In one aspect, the fermenting of the municipal solid waste material produces a fermentation product. In another aspect, the processes further comprise recovering the fermentation product from the fermentation. In preferred embodiments solubilized compounds can be converted to Biogas (mainly comprising $CH_4$ and $CO_2$) by anaerobic digestion. In other embodiments solubilized sugars can be converted to ethanol by fermentation.

The processes of the present invention can also be used to solubilize the municipal solid waste material to fermentable sugars and to convert the fermentable sugars to many useful fermentation products, e.g., fuel (ethanol, n-butanol, isobutanol, biodiesel, jet fuel) and/or platform chemicals (e.g., acids, alcohols, ketones, gases, oils, and the like). The production of a desired fermentation product from the municipal solid waste material typically involves enzymatic solubilization and fermentation.

The processing of the municipal solid waste material according to the present invention can be accomplished using methods conventional in the art. Moreover, the processes of the present invention can be implemented using any conventional biomass processing apparatus configured to operate in accordance with the invention.

Solubilization and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the municipal solid waste material to fermentable sugars, e.g., glucose, cellobiose, and pentose monomers, and then ferment the fermentable sugars to ethanol. In SSF, the enzymatic hydrolysis of the municipal solid waste material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan and Himmel, 1999, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the municipal solid waste material to fermentable sugars and to convert the fermentable sugars into a final product (Lynd et al., 2002, *Microbiol. Mol. Biol. Reviews* 66: 506-577). It is understood herein that any method known in the art comprising pretreatment, enzymatic hydrolysis, fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (de Castilhos Corazza et al., 2003, *Acta Scientiarum. Technology* 25: 33-38; Gusakov and Sinitsyn, 1985, *Enz. Microb. Technol.* 7: 346-352), an attrition reactor (Ryu and Lee, 1983, *Biotechnol. Bioeng.* 25: 53-65). Additional reactor types include fluidized bed, upflow blanket, immobilized, and extruder type reactors for hydrolysis and/or fermentation.

Pretreatment. In practicing the processes of the present invention, any pretreatment process known in the art can be used to disrupt plant cell wall components of the municipal solid waste material (Chandra et al., 2007, *Adv. Biochem. Engin./Biotechnol.* 108: 67-93; Galbe and Zacchi, 2007,

*Adv. Biochem. Engin./Biotechnol.* 108: 41-65; Hendriks and Zeeman, 2009, *Bioresource Technology* 100: 10-18; Mosier et al., 2005, *Bioresource Technology* 96: 673-686; Taherzadeh and Karimi, 2008, *Int. J. Mol. Sci.* 9: 1621-1651; Yang and Wyman, 2008, *Biofuels Bioproducts and Biorefining-Biofpr.* 2: 26-40).

In a preferred embodiment of the invention MSW is subject to a mild to severe temperature pretreatment in the range 10-300° C. prior to hydrolysis. Heating will normally occur together with a mixing. Heating will normally be carried out by addition of water or steam. Pretreatment might also consist of a separation (manual or automatic) of MSW in different fractions. The municipal solid waste material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The municipal solid waste material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The municipal solid waste material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperature in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the municipal solid waste material is subjected to physical (mechanical) or chemical pretreatment, or any combination thereof, to promote the separation and/or release of cellulose, hemicellulose, and/or lignin.

Biological Pretreatment. The term "biological pretreatment" refers to any biological pretreatment that promotes the separation and/or release of cellulose, hemicellulose, and/or lignin from the municipal solid waste material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, *Adv. Appl. Microbiol.* 39: 295-333; McMillan, J. D., 1994, Pretreating lignocellulosic biomass: a review, in Enzymatic Conversion of Biomass for Fuels Production, Himmel, M. E., Baker, J. O., and Overend, R. P., eds., *ACS Symposium Series* 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, *Enz. Microb. Tech.* 18: 312-331; and Vallander and Eriksson, 1990, *Adv. Biochem. Eng./Biotechnol.* 42: 63-95).

In other embodiments MSW can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperature in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from unds Defibrator AB, Sweden. The physical and chemical pretreatments can be carried out sequentially or simultaneously, as desired.

Hydrolysis. In the hydrolysis step, the municipal solid waste material, e.g., pretreated, is hydrolyzed to break down cellulose and/or hemicellulose and other substrates to fermentable sugars, such as glucose, cellobiose, xylose, xylulose, arabinose, mannose, galactose, and/or soluble oligosaccharides (also known as saccharification). The hydrolysis is performed enzymatically by one or more enzyme compositions in one or more stages. In the hydrolysis step, the municipal solid waste material, e.g., pretreated, is hydrolyzed to break down proteins and lipids (e.g. triglycerides) found in the waste.

The hydrolysis can be carried out as a batch process or series of batch processes. The hydrolysis can be carried out as a fed batch or continuous process, or series of fed batch or continuous processes, where the municipal solid waste material is fed gradually to, for example, a hydrolysis solution containing an enzyme composition. In an embodiment the hydrolysis a continuous hydrolysis in which a MSW material and a enzymes composition are added at different intervals throughout the hydrolysis and the hydrolysate is removed at different intervals throughout the hydrolysis. The removal of the hydrolysate may occur prior to, simultaneously with, or after the addition of the cellulosic material and the cellulolytic enzymes composition.

Enzymatic hydrolysis is preferably carried out in a suitable aqueous environment under conditions that can be readily determined by one skilled in the art. In one aspect, hydrolysis is performed under conditions suitable for the activity of the enzymes(s), i.e., optimal for the enzyme(s).

In one aspect, the saccharification is performed in the presence of dissolved oxygen at a concentration of at least 0.5% of the saturation level.

In an embodiment of the invention the dissolved oxygen concentration during saccharification is in the range of at least 0.5% up to 30% of the saturation level, such as at least 1% up to 25%, at least 1% up to 20%, at least 1% up to 15%, at least 1% up to 10%, at least 1% up to 5%, and at least 1% up to 3%. In a preferred embodiment, the dissolved oxygen concentration is maintained at a concentration of at least 0.5% up to 30% of the saturation level, such as at least 1% up to 25%, at least 1% up to 20%, at least 1% up to 15%, at least 1% up to 10%, at least 1% up to 5%, and at least 1% up to 3% during at least 25%, such as at least 50% or at least 75% of the saccharification period. When the enzyme composition comprises an oxidoreductase the dissolved oxygen concentration may be higher up to 70% of the saturation level.

Oxygen is added to the vessel in order to achieve the desired concentration of dissolved oxygen during saccharification. Maintaining the dissolved oxygen level within a desired range can be accomplished by aeration of the vessel, tank or the like by adding compressed air through a diffuser or sparger, or by other known methods of aeration. The aeration rate can be controlled on the basis of feedback from a dissolved oxygen sensor placed in the vessel/tank, or the system can run at a constant rate without feedback control. In the case of a hydrolysis train consisting of a plurality of vessels/tanks connected in series, aeration can be implemented in one or more or all of the vessels/tanks. Oxygen aeration systems are well known in the art. According to the invention any suitable aeration system may be used. Commercial aeration systems are designed by, e.g., Chemineer, Derby, England, and build by, e.g., Paul Mueller Company, MO, USA.

The enzyme compositions can comprise any protein useful in degrading the municipal solid waste material.

In one aspect, the enzyme composition comprises or further comprises one or more (e.g., several) proteins selected from the group consisting of a cellulase, an AA9 polypeptide, a hemicellulase, an esterase, an expansin, a ligninolytic enzyme, an oxidoreductase, a pectinase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. In another aspect, the oxidoreductase is preferably one or more (e.g., several) enzymes selected from the group consisting of a catalase, a laccase, and a peroxidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises an AA9 polypeptide. In another aspect, the enzyme composition comprises an endoglucanase and an AA9 polypeptide. In another aspect, the enzyme composition comprises a cellobiohydrolase and an AA9 polypeptide. In another aspect, the enzyme composition comprises a beta-glucosidase and an AA9 polypeptide. In another aspect, the enzyme composition comprises an endoglucanase and a cellobiohydrolase. In another aspect, the enzyme composition comprises an endoglucanase and a cellobiohydrolase I, a cellobiohydrolase II, or a combination of a cellobiohydrolase I and a cellobiohydrolase II. In another aspect, the enzyme composition comprises an endoglucanase and a beta-glucosidase. In another aspect, the enzyme composition comprises a beta-glucosidase and a cellobiohydrolase. In another aspect, the enzyme composition comprises a beta-glucosidase and a cellobiohydrolase I, a cellobiohydrolase II, or a combination of a cellobiohydrolase I and a cellobiohydrolase II. In another aspect, the enzyme composition comprises an endoglucanase, an AA9 polypeptide, and a cellobiohydrolase. In another aspect, the enzyme composition comprises an endoglucanase, an AA9 polypeptide, and a cellobiohydrolase I, a cellobiohydrolase II, or a combination of a cellobiohydrolase I and a cellobiohydrolase II. In another aspect, the enzyme composition comprises an endoglucanase, a beta-glucosidase, and an AA9 polypeptide. In another aspect, the enzyme composition comprises a beta-glucosidase, an AA9 polypeptide, and a cellobiohydrolase. In another aspect, the enzyme composition comprises a beta-glucosidase, an AA9 polypeptide, and a cellobiohydrolase I, a cellobiohydrolase II, or a combination of a cellobiohydrolase I and a cellobiohydrolase II. In another aspect, the enzyme composition comprises an endoglucanase, a beta-glucosidase, and a cellobiohydrolase. In another aspect, the enzyme composition comprises an endoglucanase, a beta-glucosidase, and a cellobiohydrolase I, a cellobiohydrolase II, or a combination of a cellobiohydrolase I and a cellobiohydrolase II. In another aspect, the enzyme composition comprises an endoglucanase, a cellobiohydrolase, a beta-glucosidase, and an AA9 polypeptide. In another aspect, the enzyme composition comprises an endoglucanase, a beta-glucosidase, an AA9 polypeptide, and a cellobiohydrolase I, a cellobiohydrolase II, or a combination of a cellobiohydrolase I and a cellobiohydrolase II.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In an embodiment, the xylanase is a Family 10 xylanase. In another embodiment, the xylanase is a Family 11 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a ligninolytic enzyme. In an embodiment, the ligninolytic enzyme is a manganese peroxidase. In another embodiment, the ligninolytic enzyme is a lignin peroxidase. In another embodiment, the ligninolytic enzyme is a $H_2O_2$-producing enzyme. In another aspect, the enzyme composition comprises a pectinase. In another aspect, the enzyme composition comprises an oxidoreductase. In an embodiment, the oxidoreductase is a catalase. In another embodiment, the oxidoreductase is a laccase. In another embodiment, the oxidoreductase is a peroxidase. In another aspect, the enzyme composition comprises a protease. In another aspect, the enzyme composition comprises a swollenin.

In the processes of the present invention, the enzyme(s) can be added prior to or during saccharification, saccharification and fermentation, or fermentation.

One or more (e.g., several) components of the enzyme composition may be native proteins, recombinant proteins, or a combination of native proteins and recombinant proteins. For example, one or more (e.g., several) components may be native proteins of a cell, which is used as a host cell to express recombinantly one or more (e.g., several) other components of the enzyme composition. It is understood herein that the recombinant proteins may be heterologous (e.g., foreign) and/or native to the host cell. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and polypeptides having enzymatic activity depend on several factors including, but not limited to, the mixture of cellulolytic enzymes and/or hemicellulolytic enzymes, the municipal solid waste material, the concentration of municipal solid waste material, the pretreatment(s) of the municipal solid waste material, temperature, time, pH, and inclusion of a fermenting organism (e.g., for Simultaneous Saccharification and Fermentation).

In one aspect, an effective amount of the enzyme composition to the municipal solid waste material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the municipal solid waste material. In a related aspect, the protease is present at a ratio between 0-20% w/w, such as e.g. 1, 2, 3, 4, 5, 6, 7, 8, 9, 10, 11, 12, 13, 14, 15, 16, 17, 18, 19 or 20% w/w of the total enzyme protein.

In one aspect, the beta-glucanase is present at a ratio between 0-30% w/w, such as e.g. 1, 2, 3, 4, 5, 6, 7, 8, 9, 10, 11, 12, 13, 14, 15, 16, 17, 18, 19, 20, 21, 22, 32, 24, 25, 26, 27, 28, 29 or 30% w/w of the total enzyme protein. In a related aspect, the pectate-lyase is present at a ratio between 0-10% w/w, such as e.g. 1, 2, 3, 4, 5, 6, 7, 8, 9, 10% w/w of the total enzyme protein. In a related aspect, the mannanase or amylase is present at a ratio between 0-10% w/w, such as e.g. 1, 2, 3, 4, 5, 6, 7, 8, 9, 10% w/w of the total enzyme protein. In yet another related aspect, the cellulolytic enzyme blend is present at a ratio between 40%-99% w/w, such as e.g. between 50%-90% w/w, such as e.g. 60%-80% w/w, such as e.g. 65-75% of the total enzyme protein.

The polypeptides having cellulolytic enzyme activity or hemicellulolytic enzyme activity as well as other proteins/polypeptides useful in the degradation of the municipal solid waste material, e.g., AA9 polypeptides can be derived or obtained from any suitable origin, including, archaeal, bacterial, fungal, yeast, plant, or animal origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained by, e.g., site-directed mutagenesis or shuffling.

Each polypeptide may be a bacterial polypeptide. For example, each polypeptide may be a Gram-positive bacterial polypeptide having enzyme activity, or a Gram-negative bacterial polypeptide having enzyme activity.

Each polypeptide may also be a fungal polypeptide, e.g., a yeast polypeptide or a filamentous fungal polypeptide.

Chemically modified or protein engineered mutants of polypeptides may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host can be a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes A/S), CELLIC® CTec2 (Novozymes A/S), CELLIC® CTec3 (Novozymes A/S), CELLUCLAST® (Novozymes A/S), NOVOZYM™ 188 (Novozymes A/S), SPEZYME™ CP (Genencor Int.), ACCELLERASE™ TRIO (DuPont), FILTRASE® NL (DSM); METHAPLUS® S/L 100 (DSM), ROHAMENT™ 7069 W (Röhm GmbH), or ALTERNAFUEL® CMAX3™ (Dyadic International, Inc.). The cellulolytic enzyme preparation is added in an amount effective from about 0.001 to about 5.0 wt. % of solids, e.g., about 0.025 to about 4.0 wt. % of solids or about 0.005 to about 2.0 wt. % of solids.

Examples of bacterial endoglucanases that can be used in the processes of the present invention, include, but are not limited to, *Acidothermus cellulolyticus* endoglucanase (WO 91/05039; WO 93/15186; U.S. Pat. No. 5,275,944; WO 96/02551; U.S. Pat. No. 5,536,655; WO 00/70031; WO 05/093050), *Erwinia carotovara* endoglucanase (Saarilahti et al., 1990, *Gene* 90: 9-14), *Thermobifida fusca* endoglucanase III (WO 05/093050), and *Thermobifida fusca* endoglucanase V (WO 05/093050).

Examples of fungal endoglucanases that can be used in the present invention, include, but are not limited to, *Trichoderma reesei* endoglucanase I (Penttila et al., 1986, *Gene* 45: 253-263, *Trichoderma reesei* Cel7B endoglucanase I (GenBank:M15665), *Trichoderma reesei* endoglucanase II (Saloheimo et al., 1988, *Gene* 63:11-22), *Trichoderma reesei* Cel5A endoglucanase II (GenBank:M19373), *Trichoderma reesei* endoglucanase III (Okada et al., 1988, *Appl. Environ. Microbiol.* 64: 555-563, GenBank:AB003694), *Trichoderma reesei* endoglucanase V (Saloheimo et al., 1994, *Molecular Microbiology* 13: 219-228, GenBank:Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Fusarium oxysporum* endoglucanase (GenBank: L29381), *Humicola grisea* var. *thermoidea* endoglucanase (GenBank:AB003107), *Melanocarpus albomyces* endoglucanase (GenBank:MAL515703), *Neurospora crassa* endoglucanase (GenBank:XM_324477), *Humicola insolens* endoglucanase V, *Myceliophthora thermophila* CBS 117.65 endoglucanase, *Thermoascus aurantiacus* endoglucanase I (GenBank:AF487830), *Trichoderma reesei* strain No. VTT-D-80133 endoglucanase (GenBank:M15665), and *Penicillium pinophilum* endoglucanase (WO 2012/062220).

Examples of cellobiohydrolases useful in the present invention include, but are not limited to, *Aspergillus aculeatus* cellobiohydrolase II (WO 2011/059740), *Aspergillus fumigatus* cellobiohydrolase I (WO 2013/028928), *Aspergillus fumigatus* cellobiohydrolase II (WO 2013/028928), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Penicillium occitanis* cellobiohydrolase I (GenBank:AY690482), *Talaromyces emersonii* cellobiohydrolase I (GenBank:AF439936), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydrolase II (WO 2010/057086).

Examples of beta-glucosidases useful in the present invention include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 02/095014), *Penicillium brasilianum* IBT 20888 (WO 2007/019442 and WO 2010/088387), *Thielavia terrestris* (WO 2011/035029), and *Trichophaea saccata* (WO 2007/019442).

Other useful endoglucanases, cellobiohydrolases, and beta-glucosidases are disclosed in numerous Glycosyl Hydrolase families using the classification according to Henrissat, 1991, *Biochem. J.* 280: 309-316, and Henrissat and Bairoch, 1996, *Biochem. J.* 316: 695-696.

In the processes of the present invention, any AA9 polypeptide can be used as a component of the enzyme composition.

Examples of AA9 polypeptides useful in the processes of the present invention include, but are not limited to, AA9 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290 and WO 2012/149344), *Myceliophthora thermophila* (WO 2009/085935, WO 2009/085859, WO 2009/085864, WO 2009/085868, and WO 2009/033071), *Aspergillus fumigatus* (WO 2010/138754), *Penicillium pinophilum* (WO 2011/005867), *Thermoascus* sp. (WO 2011/039319), *Penicillium* sp. (emersoni0 (WO 2011/041397 and WO 2012/000892), *Thermoascus crustaceous* (WO 2011/041504), *Aspergillus aculeatus* (WO 2012/125925), *Thermomyces lanuginosus* (WO 2012/113340, WO 2012/129699, WO 2012/130964, and WO 2012/129699), *Aurantiporus alborubescens* (WO 2012/122477), *Trichophaea saccata* (WO 2012/122477), *Penicillium thomii* (WO 2012/122477), *Talaromyces stipitatus* (WO 2012/135659), *Humicola insolens* (WO 2012/146171), *Malbranchea cinnamomea* (WO 2012/101206), *Talaromyces leycettanus* (WO 2012/101206), and *Chaetomium thermophilum* (WO 2012/101206), and *Talaromyces thermophilus* (WO 2012/129697 and WO 2012/130950).

In one aspect, the AA9 polypeptide is used in the presence of a soluble activating divalent metal cation according to WO 2008/151043, e.g., manganese or copper.

In another aspect, the AA9 polypeptide is used in the presence of a dioxy compound, a bicyclic compound, a heterocyclic compound, a nitrogen-containing compound, a quinone compound, a sulfur-containing compound, or a liquor obtained from a pretreated municipal solid waste material such as pretreated corn stover (WO 2012/021394, WO 2012/021395, WO 2012/021396, WO 2012/021399, WO 2012/021400, WO 2012/021401, WO 2012/021408, and WO 2012/021410).

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described in WO 2012/021401, and the soluble contents thereof. A liquor for cellulolytic enhancement of an AA9 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and an AA9 polypeptide during hydrolysis of a cellulosic substrate by a cellulolytic enzyme preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5 g, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC® HTec (Novozymes A/S), CELLIC® HTec2 (Novozymes A/S), CELLIC® HTec3 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740 L. (Biocatalysts Limit, Wales, UK), and DEPOL™ 762P (Biocatalysts Limit, Wales, UK), ALTERNA FUEL 100P (Dyadic), and ALTERNA FUEL 200P (Dyadic).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Thermomyces lanuginosus* (GeneSeqP: BAA22485), *Talaromyces thermophilus* (GeneSeqP: BAA22834), *Thielavia terrestris* NRRL 8126 (WO 2009/079210), and *Trichophaea saccata* (WO 2011/057083).

Examples of beta-xylosidases useful in the processes of the present invention include, but are not limited to, beta-xylosidases from *Neurospora crassa* (SwissProt:Q7SOW4), *Trichoderma reesei* (UniProtKB/TrEMBL:Q92458), *Talaromyces emersonii* (SwissProt:Q8X212), and *Talaromyces thermophilus* (GeneSeqP:BAA22816).

Examples of acetylxylan esterases useful in the processes of the present invention include, but are not limited to, acetylxylan esterases from *Aspergillus aculeatus* (WO 2010/108918), *Chaetomium globosum* (UniProt:Q2GWX4), *Chaetomium gracile* (GeneSeqP:AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt:q7s259), *Phaeosphaeria nodorum* (UniProt:QOUHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt:A1 D9T4), *Neurospora crassa* (UniProt:Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP: AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt: alcc12), *Aspergillus fumigatus* (SwissProt:Q4WW45), *Aspergillus niger* (UniProt:Q96WX9), *Aspergillus terreus* (SwissProt:Q0CJP9), *Humicola insolens* (WO 2010/014706), *Penicillium* aurantiogriseum (WO 2009/068565), *Talaromyces emersonii* (UniProt:Q8X211), and *Trichoderma reesei* (UniProt:Q99024).

Examples of oxidoreductases useful in the processes of the present invention include, but are not limited to, *Aspergillus lentilus* catalase, *Aspergillus fumigatus* catalase, *Aspergillus niger* catalase, *Aspergillus oryzae* catalase, *Humicola insolens* catalase, *Neurospora crassa* catalase, *Penicillium emersonii* catalase, *Scytalidium thermophilum* catalase, *Talaromyces stipitatus* catalase, *Thermoascus aurantiacus* catalase, *Coprinus cinereus* laccase, *Myceliophthora thermophila* laccase, *Polyporus pinsitus* laccase, *Pycnoporus cinnabarinus* laccase, *Rhizoctonia solani* laccase, *Streptomyces coelicolor* laccase, *Coprinus cinereus* peroxidase, Soy peroxidase, Royal palm peroxidase.

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, C A, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, N Y, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

In preferred embodiments, some fermentation will occur concurrent with the hydrolysis of the MSW. Fermentable sugars obtained from the hydrolyzed municipal solid waste material can be fermented by one or more (e.g., several) fermenting microorganisms capable of fermenting the sugars directly or indirectly into a fermentation products such as volatile fatty acids (e.g. acetate, propionate, butyrate), lactate and alcohols.

"Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the municipal solid waste material as a result of the pretreatment and enzymatic hydrolysis steps, are fermented to a product, e.g., ethanol, by a fermenting organism, such as yeast. Hydrolysis and fermentation can be separate or simultaneous.

Any suitable hydrolyzed municipal solid waste material can be used in the fermentation step in practicing the present invention. The material is generally selected based on economics, i.e., costs per equivalent sugar potential, and recalcitrance to enzymatic conversion.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Yeast include strains of *Candida, Kluyveromyces*, and *Saccharomyces*, e.g., *Candida sonorensis, Kluyveromyces marxianus*, and *Saccharomyces cerevisiae*.

Examples of fermenting organisms that can ferment pentose sugars in their native state include bacterial and fungal organisms, such as some yeast. Xylose fermenting yeast include strains of *Candida*, preferably *C. sheatae* or *C. sonorensis*; and strains of *Pichia*, e.g., *P. stipitis*, such as *P. stipitis* CBS 5773. Pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum*, and *Zymomonas mobilis* (Philippidis, G. P., 1996, Cellulose bioconversion technology, in *Handbook on Bioethanol: Production and Utilization*, Wyman, C. E., ed., Taylor & Francis, Washington, D.C., 179-212).

Other fermenting organisms include strains of *Bacillus*, such as *Bacillus coagulans*; *Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis*, and *C. scehatae*; *Clostridium*, such as *C. acetobutylicum, C. thermocellum*, and *C. phytofermentans*; *E. coli*, especially *E. coli* strains that have been genetically modified to improve the yield of ethanol; *Geobacillus* sp.; *Hansenula*, such as *Hansenula anomala*; *Klebsiella*, such as *K. oxytoca*; *Kluyveromyces*, such as *K. marxianus, K. lactis, K. thermotolerans*, and *K. fragilis*; *Schizosaccharomyces*, such as *S. pombe*; *Thermoanaerobacter*, such as *Thermoanaerobacter saccharolyticum*; and *Zymomonas*, such as *Zymomonas mobilis*.

In an aspect, the fermenting microorganism has been genetically modified to provide the ability to ferment pentose sugars, such as xylose utilizing, arabinose utilizing, and xylose and arabinose co-utilizing microorganisms.

In another aspect, the fermenting organism comprises one or more polynucleotides encoding one or more cellulolytic enzymes, hemicellulolytic enzymes, and accessory enzymes described herein.

It is well known in the art that the organisms described above can also be used to produce other substances, as described herein.

The fermenting microorganism is typically added to the degraded municipal solid waste material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded municipal solid waste material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2\times10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g., pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide.

In one aspect, the fermentation product is an alcohol. The term "alcohol" encompasses a substance that contains one or more hydroxyl moieties. The alcohol can be, but is not limited to, n-butanol, isobutanol, ethanol, methanol, arabinitol, butanediol, ethylene glycol, glycerin, glycerol, 1,3-propanediol, sorbitol, xylitol. See, for example, Gong et al., 1999, Ethanol production from renewable resources, in *Advances in Biochemical Engineering/Biotechnology*, Scheper, T., ed., Springer-Verlag Berlin Heidelberg, Germany, 65: 207-241; Silveira and Jonas, 2002, *Appl. Microbiol. Biotechnol.* 59: 400-408; Nigam and Singh, 1995, *Process Biochemistry* 30(2): 117-124; Ezeji et al., 2003, *World Journal of Microbiology and Biotechnology* 19(6): 595-603.

In another aspect, the fermentation product is an alkane. The alkane may be an unbranched or a branched alkane. The alkane can be, but is not limited to, pentane, hexane, heptane, octane, nonane, decane, undecane, or dodecane.

In another aspect, the fermentation product is a cycloalkane. The cycloalkane can be, but is not limited to, cyclopentane, cyclohexane, cycloheptane, or cyclooctane.

In another aspect, the fermentation product is an alkene. The alkene may be an unbranched or a branched alkene. The alkene can be, but is not limited to, pentene, hexene, heptene, or octene.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide), cell debris, biomass, fermentation media and/or fermentation products. In some embodiments, the composition is a cell-killed whole broth containing organic acid(s), killed cells and/or cell debris, and culture medium.

The term "fermentation broth" refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The fermentation broth formulations or cell compositions may further comprise multiple enzymatic activities, such as one or more (e.g., several) enzymes selected from the group consisting of a cellulase, a hemicellulase, a cellulose inducible protein (CIP), an esterase, an expansin, a laccase, a ligninolytic enzyme, a pectinase, a peroxidase, a protease, and a swollenin. The fermentation broth formulations or cell compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Examples are given below of uses of the compositions of the present invention. The dosage of the composition and other conditions under which the composition is used may be determined on the basis of methods known in the art.

Enzyme Compositions

The present invention also relates to compositions comprising a polypeptide of the present invention. Preferably, the compositions are enriched in such a polypeptide. The term "enriched" indicates that the cellobiohydrolase activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (e.g., several) enzymes selected from the group consisting of a cellulase, a hemicellulase, an AA9 polypeptide, a CIP, an esterase, an expansin, a laccase, a ligninolytic enzyme, a pectinase, a peroxidase, a protease, and a swollenin. The compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The compositions may be prepared in accordance with methods known in the art and may be in the form of a liquid or a dry composition. The compositions may be stabilized in accordance with methods known in the art.

In yet further embodiments, the enzymes of the composition of present invention may be a protease derived from *Bacillus amyloliquefaciens*, a triacylglycerol lipase with a phospho-lipase activity derived from *Thermomyces lanuginosus*, a triacylglycerol lipase derived from *Humicola insolens*, a triacylglycerol lipase derived from *Thermomyces lanuginosus*, NZ81243—a multicomponent enzyme commercially available as Novozym 81243 with pectate lyase, xylanase and cellulase activities, a beta-glucanase derived from *Aspergillus aculeatus*. an alpha-amylase derived from *Rhizomucor pusillus* and/or an endo-mannosidase derived from *Bacillus bogoriensis*.

Examples are given below of uses of the compositions of the present invention. The dosage of the composition and other conditions under which the composition is used may be determined on the basis of methods known in the art.

Materials and Methods

1. Substrate Preparation

Unsorted MSW is basically made up of two solid fractions: 1) Inorganic non-degradables consisting of plastic, glass, metal etc. and 2) Degradable organics consisting of vegetable, animal waste, food waste, paper, cardboard etc. As an example the latter part typically makes up approximately 65-70% of the incoming waste in Denmark (for a detailed composition analysis see Riber et al. 2009, Waste Management 29, p. 1251-1257).

The scope of the experiments described below was to optimize the solubilization of the degradable organic parts of MSW. Therefore, we choose to use a model waste that reflected the composition of degradable organics in MSW as described by Riber et al. 2009. The model waste consisted of 3 fractions based on fresh products supplemented with water:

- 40.1% Vegetable origin. Mix of fresh vegetables (onions, cabbage, carrots, cucumber etc.), cereals (oatmeals, corn flakes etc.), bread, cake, flowers, boiled rice, boiled pasta fruit, ketchup etc.
- 11.3% Animal origin. Mix of pâté, sausage, hotwings, spareribs, crude meats from chicken, pork and beef etc.
- 36.2% Cellulose origin. Mix of newsprints, office paper, magazines, cardboard, juice cartons, kitchen tissue, cotton, wood, textiles etc.
- Water to obtain a consistency of the model waste suitable in the assays (described later).

A total of 3 different batches were used prepared and used for the experiments. Batch 1 and 2 was prepared by REnescience (DONG NS). Batch 3 was prepared in our own laboratories. The composition of the model waste is given in the table below:

| Total solids/dry matter (TS) | 25.2-28.3% |
|---|---|
| TS composition: | |
| Klason lignin | 12% |
| Cellulose | 29-32% |
| Xylan | 10% |
| Arabinan | 1% |
| Galactan | 1.7% |
| Mannnan | 4% |
| Fats | 7% |
| Protein | 7-8% |
| Starch | 3-10% |
| Ash | 15% |

2. Assay for Enzymatic Solubilization of Model Waste in Bench Scale.

If not otherwise stated, experiments were carried out on a 20 g scale. A standard assay for enzymatic solubilization of model waste was used as follows:
1. 50 ml centrifuge tubes+lid were weighed.
2. Model waste was added to the tubes (total of 1.5 g TS).
3. 50 mM citric acid buffer (pH 5) (app. 14.7 ml) and enzymes was added (total weight=20 g and 7.5% TS) and tubes was vigorously shaken.
4. Tubes were incubated on a Stuart Rotator SB3 at 12 rpm in ovens at 50° C. for 24 hours.
5. After incubation, 0.4 ml 10% proxel was added to kill lactic acid bacteria and other microorganisms.
6. The tubes were centrifuged 10 min at 2090×g.
7. A new set of 50 ml tubes were weighed but without lids, marked as supernatant.
8. Supernatant was poured in the tubes and the tubes+sup was weighed.
9. Approx. 2×1.5 ml of supernatant was removed and poured in eppendorf tubes for analysis. 50 ml tubes with supernatant were weighed again.
11. The first tube+pellet were weighed again.
12. Eppendorf tubes with supernatant were stored in freezer.
13. TS of the supernatant and pellet were determined by drying the tubes at 50° C. The tubes was weighed and then dried at 105° C. and weighed again.

Analysis: Mass balances based on weight were made before and after incubation. If more than 5% of the substrate had been lost samples were discarded. The ratio of the dry matter content in the supernatant and pellet following centrifugation was calculated for all samples. If needed, samples that had been frozen were analyzed for sugar content, acetic acid and lactate on HPLC.

EXAMPLES

Example 1

Screening of Individual Enzymes and Selection of Enzyme Candidates for Blending.

Initially, a very broad range of enzymes (>50; Novozymes A/S, Bagsværd, Denmark) were screened for investigating the potential of improving the hydrolysis of the model waste. The tested enzymes included alpha-amylases, gluco-amylase, pullulanase, proteases, lipases, cellulases, xylanases, pectinases and beta-glucanases.

The described standard assay was used. Control vials were added CBC (CELLIC® Ctec3; Novozymes A/S, Bagsværd, Denmark) in an amount of 2.4%/TS (product to dry matter). In test vials part of CBC was replaced with other enzymes on a protein:protein basis in different ratios ranging from 1-50%. Density of CBC and different products was taken into account. Furthermore, blanks with substrate and buffer but no enzymes were prepared. All tests were carried out in at least duplicates.

The primary success criteria for an improved hydrolysis were defined as an increase in soluble total solids (TS in supernatant). The ratio of TS-solubilisation during the screening procedure was in general around 25-28% for samples with CBC but variations were seen. The TS-solubilisation of tubes without enzymes was consistent around 10-11%. Candidates were selected for further testing:
- B.a protease (SEQ ID NO: 1): A protease derived from *Bacillus amyloliquefaciens* that gave up to 5% increase in TS-solubilization at 30% replacement of CBC.
- T.l pholip (SEQ ID NO: 2): A triacylglycerol lipase with phospho-lipase activity derived from *Thermomyces*

*lanuginosus* that gave up to 4.4-8.5% increase in TS-solubilization at 2-20% replacement of CBC.

H.i trilip (H.i trilip): A triacylglycerol lipase derived from *Humicola insolens* that gave up to 4-7% increase in TS-solubilization at 5-20% replacement of CBC.

T.l trilip (SEQ ID NO: 3): A triacylglycerol lipase derived from *Thermomyces lanuginosus* that gave up to 10-15% increase in TS-solubilization at 1-10% replacement of CBC.

NZ81243 A multicomponent enzyme commercially available as Novozym 81243 with pectate lyase, xylanase and cellulase activities. Gave up to 4% increase in TS solubilization at 5-20% replacement of CBC. 2:1

A.a BG: (SEQ ID NO: 4): A beta-glucanase derived from *Aspergillus aculeatus*. Contains side activities (cellulase, xylanases, pectinase). Gave up to 6.2-8.2% increase in TS solubilization at 20-40% replacement of CBC. Gave up to 16% in TS solubilization at 30% replacement of CBC when mixed with NZ81243 in a 2:1 ratio.

R.p Alam (SEQ ID NO: 5): A alpha-amylase derived from *Rhizomucor pusillus* that improve glucose yields in the supernatant with up to 20% at 5-20% replacement of CBC.

B.b Enma: An endo-mannosidase derived from *Bacillus bogoriensis*. Gave up to 6-10% increase in TS solubilization at 2.5-10% replacement of CBC.

Example 2

Designing of Optimized Enzymes Mix by Blending of Selected Candidates

Statistical experiments were setup to find the optimal ratio between CBC and the selected enzymes candidates in a multicomponent enzymes blend. Based on the screening experiments we decided to use two different templates that specified the enzymes ratios to be used:

For both templates it was decided to use 0-20% B.a protease (protease) and 0-10% lipase. This was supplemented with either a) 0-30% A.a BG (beta-glucanase)+/− NZ81243 (pectate lyase) or b) 0-20% B.b Enma (endo-mannosidase) or 0-20% R.p Alam (alpha-amylase). A total of 6 blending experiments were performed.
Experiment a.1-a.3.

The initial three experiments were carried out to select the most suitable lipase when combined with 0-20% B.a protease and 0-30% A.a BG. The templates were as follows:
Blend Template a.1

| Enzyme Name | Ratio of total enzyme protein: |
|---|---|
| B.a protease | 0-20% |
| T.l pholip | 0-10% |
| A.a BG | 0-30% |
| CBC | Supplement to 100% |

Blend Template a.2

| Enzyme Name | Ratio of total enzyme protein: |
|---|---|
| B.a protease | 0-20% |
| T.l trilip | 0-10% |
| A.a BG | 0-30% |
| CBC | Supplement to 100% |

Blend Template a.3

| Enzyme Name | Ratio of total enzyme protein: |
|---|---|
| B.a protease | 0-20% |
| H.i trilip | 0-10% |
| A.a BG | 0-30% |
| CBC | Supplement to 100% |

Statistical discovery software (Design Of Experiments, DOE) by JMP® was used to design the dosing in the experiment (see table below). As in Example 1, the enzymes concentration in control vials (vial 17 and 39) was 2.4% CBC/TS. In test vials part of CBC was replaced with other enzymes on a protein:protein basis as stated in the table below. Each test blend was carried out in duplicates.

Enzymes Dosing in Tubes. Used for Template a.1, a.2, a.3. a.4. a.5.

| Tube # | CBC | B.a protease | T.l pholip or T.l trilip or H.i trilip | A.a BG |
|---|---|---|---|---|
| | | | Ratio ( % of enzyme protein) | |
| 12 | 0.4 | 0.2 | 0.1 | 0.3 |
| 22 | 0.4 | 0.2 | 0.1 | 0.3 |
| 6 | 0.5 | 0.2 | 0 | 0.3 |
| 19 | 0.5 | 0.1 | 0.1 | 0.3 |
| 21 | 0.5 | 0.1 | 0.1 | 0.3 |
| 25 | 0.5 | 0.2 | 0 | 0.3 |
| 10 | 0.55 | 0.2 | 0.1 | 0.15 |
| 26 | 0.55 | 0.2 | 0.1 | 0.15 |
| 9 | 0.6 | 0 | 0.1 | 0.3 |
| 13 | 0.6 | 0.1 | 0 | 0.3 |
| 29 | 0.6 | 0.1 | 0 | 0.3 |
| 36 | 0.6 | 0 | 0.1 | 0.3 |
| 3 | 0.65 | 0 | 0.05 | 0.3 |
| 4 | 0.65 | 0.2 | 0 | 0.15 |
| 28 | 0.65 | 0 | 0.05 | 0.3 |
| 33 | 0.65 | 0.2 | 0 | 0.15 |
| 2 | 0.7 | 0.2 | 0.1 | 0 |
| 5 | 0.7 | 0.1 | 0.05 | 0.15 |
| 15 | 0.7 | 0 | 0 | 0.3 |
| 23 | 0.7 | 0.1 | 0.05 | 0.15 |
| 24 | 0.7 | 0.2 | 0.1 | 0 |
| 35 | 0.7 | 0 | 0 | 0.3 |
| 7 | 0.75 | 0.2 | 0.05 | 0 |
| 16 | 0.75 | 0 | 0.1 | 0.15 |
| 30 | 0.75 | 0 | 0.1 | 0.15 |
| 31 | 0.75 | 0.2 | 0.05 | 0 |
| 8 | 0.8 | 0.2 | 0 | 0 |
| 11 | 0.8 | 0.1 | 0.1 | 0 |
| 37 | 0.8 | 0.2 | 0 | 0 |
| 38 | 0.8 | 0.1 | 0.1 | 0 |
| 14 | 0.85 | 0 | 0 | 0.15 |
| 34 | 0.85 | 0 | 0 | 0.15 |
| 18 | 0.9 | 0 | 0.1 | 0 |
| 20 | 0.9 | 0.1 | 0 | 0 |
| 27 | 0.9 | 0 | 0.1 | 0 |
| 32 | 0.9 | 0.1 | 0 | 0 |
| 1 | 0.95 | 0 | 0.05 | 0 |
| 40 | 0.95 | 0 | 0.05 | 0 |
| 17 | 1 | 0 | 0 | 0 |
| 39 | 1 | 0 | 0 | 0 |

The highlights of test a.1, a.2 and a.3 are given in the tables below:

Results Highlights Blend a.1

| Enzyme components | B.a protease, T.l pholip, A.a BG, CBC |
|---|---|
| Result control (TS solubilization) | 25.8% |
| 1. best blend (TS solubilization) | 32.8% |

-continued

| Enzyme components | B.a protease, T.I pholip, A.a BG, CBC |
|---|---|
| Improvement | 27.1% |
| Best ratio between enzymes | 10:5:15:70 |
| 2. best blend (TS solubilization) | 30.8% |
| Improvement | 19.4% |
| Best ratio between enzymes | 10:10:0:80 |
| Best ratio according to model | 13:7:11:69 |

Results Highlights Blend a.2

| Enzyme components | B.a protease, T.I trilip, A.a BG, CBC |
|---|---|
| Result control (TS solubilization) | 28.1% |
| 1. best blend (TS solubilization) | 34.7% |
| Improvement | 23.5% |
| Best ratio between enzymes | 20:10:30:40 |
| 2. best blend (TS solubilization) | 33.4% |
| Improvement | 18.9% |
| Best ratio between enzymes | 10:10:0:80 |

Results Highlights Blend a.3

| Enzyme components | B.a protease, H.i trilip, A.a BG, CBC |
|---|---|
| Result control (TS solubilization) | 26.1% |
| 1. best blend (TS solubilization) | 32.5% |
| Improvement | 24.5% |
| Best ratio between enzymes | 10:5:15:70 |
| 2. best blend (TS solubilization) | 31.9% |
| Improvement | 22.2% |
| Best ratio between enzymes | 20:5:0:80 |

As shown, the best improvement over CBC in TS-solubilization was found in experiment a.1 with a 27.1% increase with a ratio of 10:5:15:70 for B.a protease:T.l pholip:A.a BG:CBC. Interestingly, the TS-solubilization in the individual vials showed significant deviations ranging from a slight negative impact by the enzymes mix to a pronounced boost of +30.4% in tube number 23. As written in Example 1, the individual improvements of B.a protease, T.l pholip and A.a BG was up to 5%, 8.5% and 8.2% respectively. Multiplication of the individual effects only adds up to 21.7%. Thus, a synergistic effect was clearly obtained in experiment a.1 when mixing the enzymes.

Clear improvements in TS solubilization was also seen in experiment a.2 (up to 23.5% with a combination of B.a protease:T.l trilip:A.a BG:CBC in a ratio of 20:10:30:40) and a.3 (up to 24.5% with a combination of B.a protease:H.i trilip:A.a BG:CBC in a ratio of 10:5:15:70). It was however decided to continue with T.l pholip in the following experiments.

Experiment a.4.

This experiment was used to decide whether A.a BG should be supplemented with NZ81243. The initial screening (Example 1) had shown a boost in TS solubilization when the two enzymes was combined.

Blend Template a.4

| Enzyme Name | Ratio of total enzyme protein: |
|---|---|
| B.a protease | 0-20% |
| T.I pholip | 0-10% |
| A.a BG + NZ81243 (2:1 mix) | 0-30% |
| CBC | Supplement to 100% |

As shown in the table below, TS-solubilization could be increased to 22.1%. However, this was a smaller improvement than in experiment a.1 where A.a BG was not supplemented with NZ81243.

Results Highlights Blend a.4

| Enzyme components | B.a protease, T.I pholip, A.a BG + NZ81243, CBC |
|---|---|
| Result control (TS solubilization) | 26.6% |
| 1. best blend (TS solubilization) | 32.5% |
| Improvement | 22.1% |
| Best ratio between enzymes | 0:5:30:65 |
| 2. best blend (TS solubilization) | 32.3% |
| Improvement | 21.4% |
| Best ratio between enzymes | 20:5:0:75 |

Experiment b.1. and b.2.

This experiment was used to decide whether the alpha amylase R.p Alam or endo-mannosidase B.b Enma where a better "match" for the protease B.a protease and the lipase T.l pholip than A.a BG.

The following blend and dosing templates were used:

Blend Template b.1

| Enzyme Name | Ratio of total enzyme protein: |
|---|---|
| B.a protease | 0-20% |
| T.I pholip | 0-10% |
| B.b Enma | 0-10% |
| CBC | Supplement to 100% |

Blend Template b.2

| Enzyme Name | Ratio of total enzyme protein: |
|---|---|
| B.a protease | 0-20% |
| T.I pholip | 0-10% |
| R.p Alam | 0-10% |
| CBC | Supplement to 100% |

Enzymes Dosing in Tubes. Used for Template b.1, b.2.

| Tube # | CBC | B.a protease | T.I pholip | B.b Enma or R.p Alam |
|---|---|---|---|---|
| | | Ratio ( % of enzyme protein) | | |
| 15 | 0.6 | 0.2 | 0.1 | 0.1 |
| 37 | 0.6 | 0.2 | 0.1 | 0.1 |
| 10 | 0.65 | 0.2 | 0.05 | 0.1 |
| 17 | 0.65 | 0.2 | 0.1 | 0.05 |
| 27 | 0.65 | 0.2 | 0.1 | 0.05 |
| 40 | 0.65 | 0.2 | 0.05 | 0.1 |
| 3 | 0.7 | 0.1 | 0.1 | 0.1 |
| 5 | 0.7 | 0.2 | 0 | 0.1 |
| 8 | 0.7 | 0.2 | 0.1 | 0 |
| 29 | 0.7 | 0.2 | 0 | 0.1 |
| 30 | 0.7 | 0.1 | 0.1 | 0.1 |
| 35 | 0.7 | 0.2 | 0.1 | 0 |
| 16 | 0.75 | 0.2 | 0.05 | 0 |
| 20 | 0.75 | 0.2 | 0 | 0.05 |

| Tube # | CBC | B.a protease | T.l pholip | B.b Enma or R.p Alam |
|---|---|---|---|---|
| | | Ratio ( % of enzyme protein) | | |
| 26 | 0.75 | 0.2 | 0.05 | 0 |
| 28 | 0.75 | 0.2 | 0 | 0.05 |
| 13 | 0.8 | 0.1 | 0.1 | 0 |
| 14 | 0.8 | 0 | 0.1 | 0.1 |
| 18 | 0.8 | 0.1 | 0.05 | 0.05 |
| 19 | 0.8 | 0.2 | 0 | 0 |
| 31 | 0.8 | 0.2 | 0 | 0 |
| 33 | 0.8 | 0.1 | 0.1 | 0 |
| 34 | 0.8 | 0 | 0.1 | 0.1 |
| 38 | 0.8 | 0.1 | 0.05 | 0.05 |
| 4 | 0.85 | 0 | 0.05 | 0.1 |
| 12 | 0.85 | 0 | 0.1 | 0.05 |
| 32 | 0.85 | 0 | 0.05 | 0.1 |
| 39 | 0.85 | 0 | 0.1 | 0.05 |
| 2 | 0.9 | 0 | 0 | 0.1 |
| 6 | 0.9 | 0 | 0.1 | 0 |
| 9 | 0.9 | 0.1 | 0 | 0 |
| 21 | 0.9 | 0 | 0.1 | 0 |
| 24 | 0.9 | 0 | 0 | 0.1 |
| 25 | 0.9 | 0.1 | 0 | 0 |
| 1 | 0.95 | 0 | 0 | 0.05 |
| 7 | 0.95 | 0 | 0.05 | 0 |
| 22 | 0.95 | 0 | 0.05 | 0 |
| 23 | 0.95 | 0 | 0 | 0.05 |
| 11 | 1 | 0 | 0 | 0 |
| 36 | 1 | 0 | 0 | 0 |

Results Highlights Blend b.1

| Enzyme components | B.a protease, T.l pholip, B.b Enma, CBC |
|---|---|
| Result control (TS solubilization) | 27.4% |
| 1. best blend (TS solubilization) | 34.0% |
| Improvement | 24.1% |
| Best ratio between enzymes | 20:0:30:50 |
| 2. best blend (TS solubilization) | 33.1% |
| Improvement | 20.8% |
| Best ratio between enzymes | 20:5:10:65 |

Results Highlights Blend b.2

| Enzyme components | B.a protease, T.l pholip, R.p Alam, CBC |
|---|---|
| Result control (TS solubilization) | 25.7% |
| 1. best blend (TS solubilization) | 30.7% |
| Improvement | 19.4% |
| Best ratio between enzymes | 0:5:30:60 |
| 2. best blend (TS solubilization) | 30.3% |
| Improvement | 17.9% |
| Best ratio between enzymes | 20:5:0:75 |

In both blending experiments an improved performance in TS-solubilization was found when compared to CBC, but all test were inferior to the blend ratio found in experiment a.1 where B.a protease, T.l pholip, A.a BG, where mixed with CBC in a ratio of 10:5:15:70.

Based on these observations it was decided to use this enzymes combination in the further development.

Example 3

Testing the Selected Enzymes Blend and CELLIC® Ctec3 in Free Fall Experiments at Elevated Dry Matter Concentration.

An experiment was carried out to test the efficiency of the selected enzymes blend at a dry matter concentration that was higher than during the screening and blending experiments. However, due to a high viscosity of model waste, mixing is not optimal in 50 ml tubes when experiments are carried at dry matter concentrations above 7.5%. Instead, experiments were performed in 100 ml Kautex bottles. Model waste was mixed with water to a volume of 50 ml and at TS concentration of 7.5% and 15%. CBC and the selected blend (B.a protease:T.l pholip:A.a BG:CBC in ratio of 10:5:15:70) were added in an amount of 2.4%/TS (product to dry matter CBC). Tubes were incubated for 24 hours at 50° C. in the tumbler-reactor. Results are shown in FIG. 1.

TS solubilization of original biomass in control tubes (no enzymes) were 10.9% and 3.2% at 7.5% and 15%, respectively. Addition of CBC improved TS-solubilization to 29.6% and 25.8. Supplementing CBC with the other enzymes improved solubilization further to 37.1 and 30.7%. This corresponds to a relative improvement of 25.7% (7.5% dry matter) and 18.9% (15% dry matter), when comparing the blend with CBC. The numbers obtained at 7.5% dry matter confirms the improvement seen in 20 g scale (50 ml tubes), which was up to 27.3%.

Example 4. Comparable Dose-Response Experiments with CBC and the Enzymes Blend

Experiments were performed in 100 ml Kautex bottles. Model waste was mixed with water to a volume at 50 ml and at TS concentration of 7.5%. CBC and the selected blend (B.a protease:T.l pholip:A.a BG:CBC in ratio of 10:5:15:70) were added in amounts corresponding to 0%, 25%, 50%, 75%, 100% and 200% of the concentration that has been used as default during the previous experiments (2.4% enzymes protein/TS). Bottles were incubated on a Stuart Rotator SB3 and placed in a 50° C. oven for 24 hours.

Figure 2:
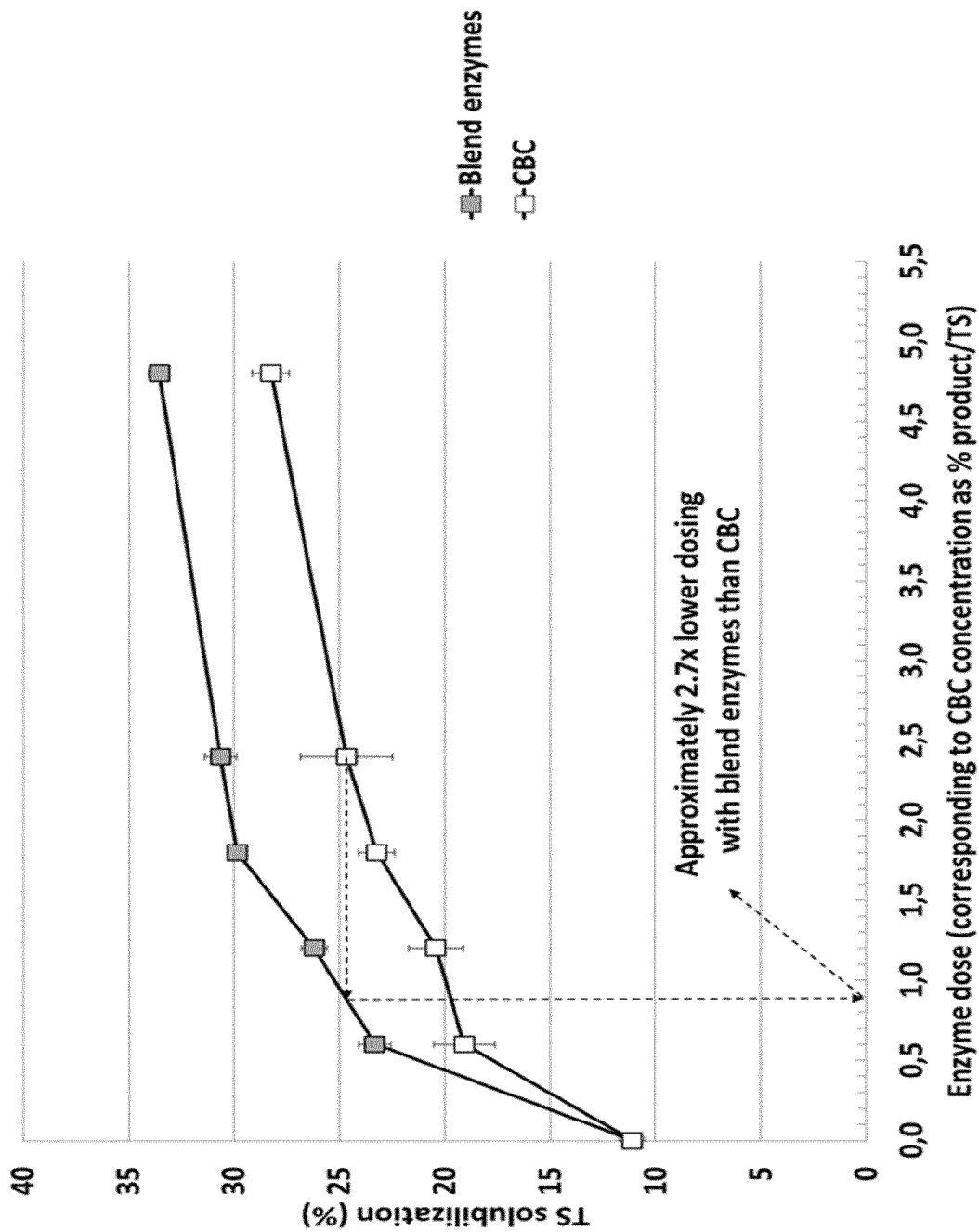
FIG. 2 shows a plot of data from dose response experiments with blend enzymes and CBC and model waste. The figure illustrates the dry matter found in the liquid fraction (TS solubilization) at different enzymes concentration.
Figure 3:
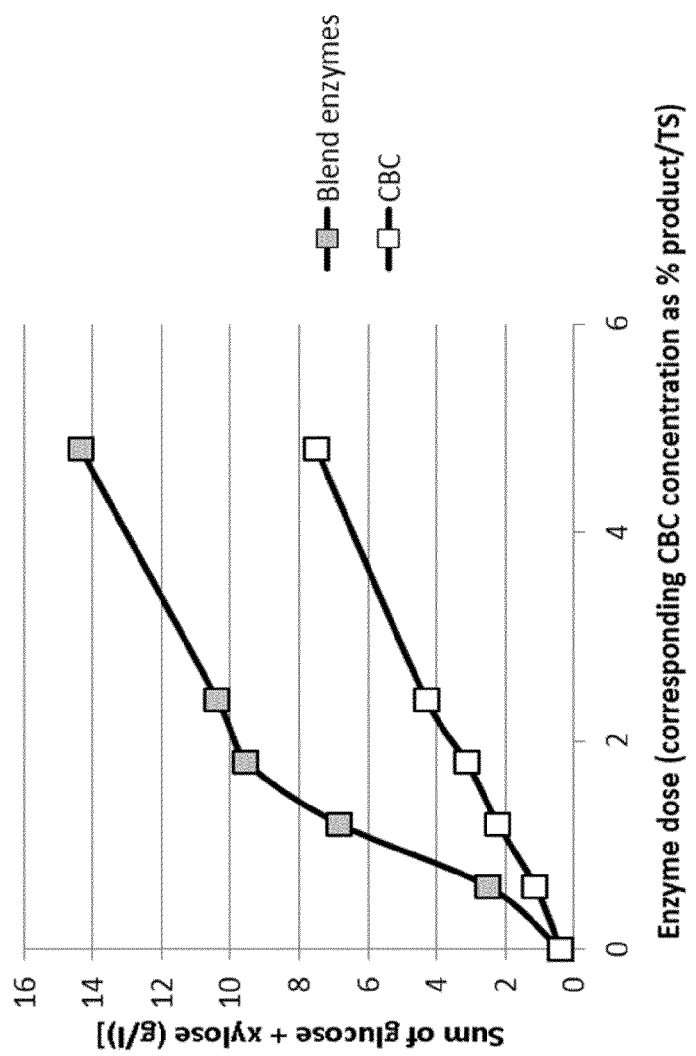
FIG. 3 shows a plot of data from dose response experiments with blend enzymes and CBC and model waste. The figure illustrates sum of glucose and xylose (g/l) at different enzymes concentration.

A significant improvement in TS-solubilization was seen at all applied enzyme concentrations, when comparing the blend with CBC. The TS-solubilization at default settings (2.4% CBC/TS) was around 25%. This was obtained with only approximately 0.9% of the blend, which corresponds to a lowering in enzyme dosage of approximately 2.5 to 2.7 times (See FIG. 2). At the same time we found a clear increase in hydrolysis and fermentation products such as glucose, xylose, lactic acid (FIG. 3, and FIG. 5). This is a surprise since 15% of CBC (cellulase and xylanase activities) was replaced with the lipase and protease.

Example 5

Omitting Individual Components from Blend

An experiment was carried out to test the relevance of the individual enzymes in the optimized blend (B.a protease:T.l pholip:A.a BG:CBC in ratio of 10:5:15:70). The setup of control vials was as described in Example 1 (2.4% CELLIC® Ctec, 7.5% TS, 20 gram scale). In test vials the optimized blend was applied, including all enzymes. At the same time test vials were made were either B.a protease, T.l pholip or A.a BG had been excluded from the blend.

Figure 4:
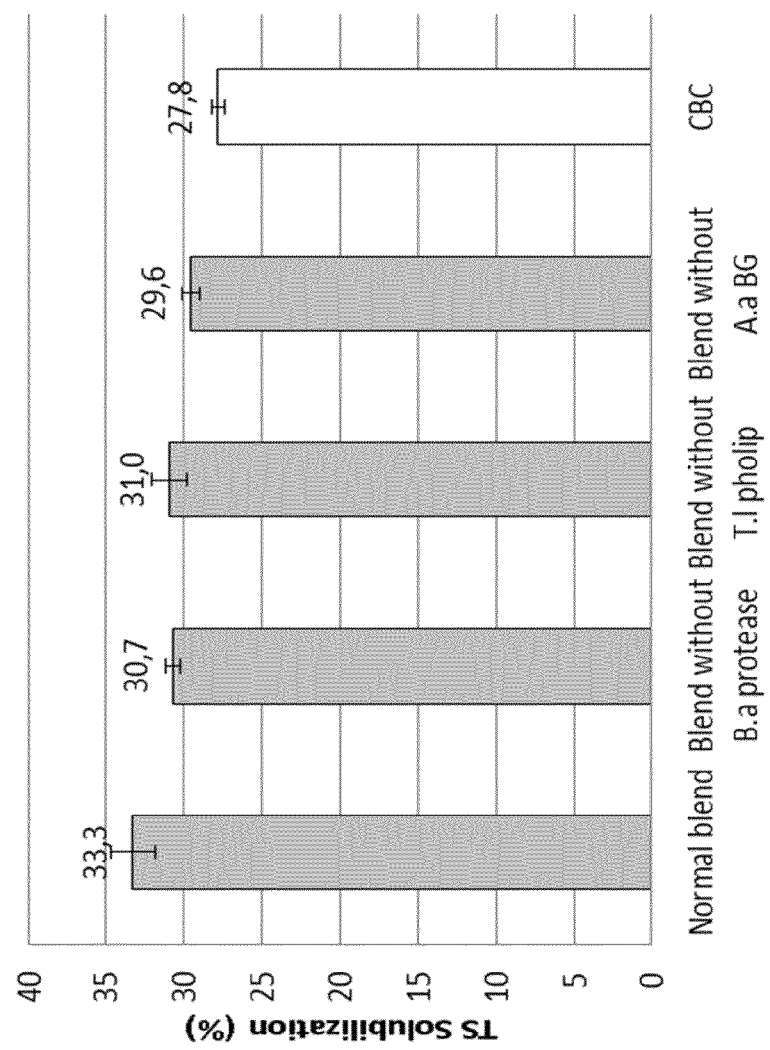
FIG. 4 shows a graph illustrating the effect of removing either B.a protease, T.l pholip or A.a BG components from the optimized blend. The figure illustrates the dry matter found in the liquid fraction (TS solubilization).

The effect on TS-solubilization is illustrated in FIG. 4 and clearly shows that removing any of the individual enzymes resulted in a lower TS-solubilization, when compared to vials with all enzymes. However, when only using two (2) of the selected enzymes to supplement CBC (T.l pholip+A.a BG, B.a protease+A.a BG, B.a protease+T.l pholip) we still observed an improved TS-solubilization, when compared to vials with only CBC, even though total enzymes protein concentration had been lowered by removing individual enzymes.

Although the foregoing has been described in some detail by way of illustration and example for the purposes of clarity of understanding, it is apparent to those skilled in the art that any equivalent aspect or modification, may be practiced. Therefore, the description and examples should not be construed as limiting the scope of the invention.

The present invention may be further described by the following numbered paragraphs:

[1] An enzyme composition for solubilization of Municipal Solid Waste (MSW), the enzyme composition comprising: (i) a cellulolytic background composition and (ii) a protease; and/or (iii) a lipase.

[2] The composition of paragraph [1], further comprising (iv) a beta-glucanase; (v) a pectate lyase; (vi) a mannanase and/or (vii) an amylase.

[3] The composition of paragraph [1] or [2], wherein the cellulolytic background composition comprises a) a cellobiohydrolase I or variant thereof; (b) cellobiohydrolase II or variant thereof; (c) beta-glucosidase or variant thereof; and (d) a polypeptide having cellulolytic enhancing activity; or homologs thereof.

[4] The composition of any of paragraphs [1] to [3], wherein the cellulolytic background composition comprise (a) an *Aspergillus fumigatus* cellobiohydrolase I or variant thereof; (b) an *Aspergillus fumigatus* cellobiohydrolase II or variant thereof; (c) an *Aspergillus fumigatus* beta-glucosidase or variant thereof; and (d) a *Penicillium* sp. GH61 polypeptide having cellulolytic enhancing activity; or homologs thereof.

[5] The composition of any of paragraphs [1] to [4], wherein the (ii) a protease is derived from the genus *Bacillus*, such as e.g. *Bacillus amyloliquefaciens* such as e.g. the protease encoded by SEQ ID NO: 1.

[6] The composition of any of paragraphs [1] to [5], wherein the (iii) a lipase is derived from the genus *Thermomyces* sp. such as e.g. *Thermomyces lanuginosus* such as e.g. the lipase encoded by SEQ ID NO: 2 or wherein the (ii) a lipase is derived from the genus *Humicola* sp. such as e.g. *Humicola insolens*.

[7] The composition of any of paragraphs [1] to [6], wherein the (iv) a beta-glucanase is derived from a member of the genus *Aspergillus* such as e.g. *Aspergillus aculeatus* such as e.g. the beta-glucanase encoded by the sequence encoded by SEQ ID NO: 4 or homologs thereof.

[8] The composition of any of paragraphs [1] to [7], wherein the (v) a pectate lyase forms part of a multicomponent enzyme composition comprising pectate lyase, xylanase and cellulase activities such as e.g. Novozym 81243™.

[9] The composition of any of paragraphs [1] to [8], wherein the (vi) a mannanase is an endo-mannosidase derived from the genus *Bacillus* such as e.g. *Bacillus bogoriensis* such as e.g. the endo-mannosidase encoded by SEQ ID NO: 6 or homologs thereof.

[10] The composition of any of paragraphs [1] to [9], wherein the (vii) an amylase is an alpha-amylase derived from the genus *Rhozimucor* such as e.g. *Rhizomucor pusillus* such as e.g. the alpha-amylase encoded by SEQ ID NO: 5 or homologs thereof.

[11] The composition of any of paragraphs [1] to [10], wherein the protease is present at a ratio between 0-20% w/w, such as e.g. 10% w/w of the total enzyme protein.

[12] The composition of any of paragraphs [1] to [11], wherein the beta-glucanase is present at a ratio between 0-30% w/w, such as e.g. 15% w/w of the total enzyme protein.

[13] The composition of any of paragraphs [1] to [12], wherein the pectate-lyase is present at a ratio between 0-10% w/w, such as e.g. 5% w/w of the total enzyme protein.

[14] The composition of any of paragraphs [1] to [13], wherein the mannanase or amylase is present at a ratio between 0-10% w/w, such as e.g. 5% w/w of the total enzyme protein.

[15] The composition of any of paragraphs [1] to [14], wherein the cellulolytic enzyme blend is present at a ratio between 40%-99% w/w, such as e.g. between 50%-90% w/w, such as e.g. 60%-80% w/w, such as e.g. 65-75% of the total enzyme protein.

[16] The composition of any of paragraphs [1] to [15], wherein the enzyme composition further comprises one or more enzymes selected from the group consisting of a cellulase, an AA9 polypeptide, a hemicellulase, a cellulose inducible protein (CIP) an esterase, an expansin, a ligninolytic enzyme, an oxidoreductase, a pectinase, a protease, and a swollenin.

[17] The composition of any of paragraphs [1] to [16], wherein the hemicellulase is one or more enzymes selected from the group consisting of a xylanase, an acetylxylan esterase, a feruloyl esterase, an arabinofuranosidase, a xylosidase, and a glucuronidase.

[18] A process for solubilizing waste comprising:
(a) contacting waste with the enzyme composition of any of paragraphs [1]-[17].

[19] The process of paragraph [18], wherein the waste is Municipal Solid Waste (MSW).

[20] A process for producing a fermentation product, comprising:
(a) treating MSW with the enzyme composition of any of paragraphs [1]-[17]
(b) fermenting the solubilized and/or hydrolysed MSW with one or more fermenting microorganisms to produce a fermentation product; and
(c) recovering the fermentation product from the fermentation.

[21] The process of any of paragraphs [18]-[20], wherein the waste is pretreated.

What is claimed is:

1. A process for solubilizing Municipal Solid Waste (MSW) comprising:
   (a) contacting the MSW with an enzyme composition comprising a cellulolytic background composition present at a ratio between 40-99% w/w of the total enzymes protein, a lipase present at a ratio between 2.5-7.5% w/w of the total enzymes protein, wherein the lipase is derived from *Thermomyces lanuginosus*, or wherein the lipase is a triacylglycerol lipase derived from *Humicola insolens*; and one or more enzymes selected from (i) a protease present at a ratio between 0-20% w/w of the total enzymes protein, wherein the protease is derived from *Bacillus amyloliquefaciens*; and (ii) a beta-glucanase present at a ratio between 0-30% w/w of the total enzymes protein, wherein the beta-glucanase is derived from *Aspergillus aculeatus*, in order to produce solubilized and/or hydrolysed MSW.

2. The process of claim 1, wherein the enzyme composition further comprises one or more enzymes selected from (iii) a pectate lyase; (iv) a mannanase; and (v) an amylase.

3. The process of claim 1, wherein the cellulolytic background composition comprises one or more enzymes selected from (a) a cellobiohydrolase I or variant thereof, (b) cellobiohydrolase II or variant thereof, (c) beta-glucosidase or variant thereof, and (d) a polypeptide having cellulolytic enhancing activity; or homologs thereof.

4. The process of claim 1, wherein the cellulolytic background composition comprises (a) a cellobiohydrolase I or variant thereof; (b) cellobiohydrolase II or variant thereof; (c) beta-glucosidase or variant thereof; and (d) a polypeptide having cellulolytic enhancing activity; or homologs thereof.

5. The process of claim 3, wherein the cellobiohydrolase I of (a) is an *Aspergillus fumigatus* cellobiohydrolase I or variant thereof; the cellobiohydrolase II of (b) is an *Aspergillus fumigatus* cellobiohydrolase II or variant thereof; the beta-glucosidase of (c) is an *Aspergillus fumigatus* beta-glucosidase or variant thereof; and the polypeptide having cellulolytic enhancing activity of (d) is a *Penicillium* sp. GH61 polypeptide having cellulolytic enhancing activity; or homologs thereof.

6. The process of claim 1, wherein the protease (i) of the enzyme composition has at least 90% sequence identity to SEQ ID NO: 1.

7. The process of claim 1, wherein the lipase of the enzyme composition has at least 90% sequence identity to SEQ ID NO: 2 or SEQ ID NO: 3.

8. The process of claim 1, wherein the beta-glucanase (ii) of the enzyme composition is encoded by a sequence having at least 90% sequence identity to SEQ ID NO: 4.

9. The process of claim 2, wherein the pectate lyase (iii) of the enzyme composition forms part of a multicomponent enzyme composition comprising pectate lyase, xylanase and cellulase activities.

10. The process of claim 2, wherein the mannanase (iv) of the enzyme composition is an endo-mannosidase derived from the genus *Bacillus* and is encoded by a sequence having at least 90% sequence identity to SEQ ID NO: 6.

11. The process of claim 2, wherein the amylase (v) of the enzyme composition is an alpha-amylase derived from the genus *Rhizomucor* and is encoded by a sequence having at least 90% sequence identity to SEQ ID NO: 5.

12. The process of claim 2, wherein
a) the protease of the enzyme composition is present at a ratio between 5-15% w/w of the total enzymes protein;
b) the lipase of the enzyme composition is present at a ratio between 2.5-7.5% w/w of the total enzyme protein;
c) the beta-glucanase of the enzyme composition is present at a ratio between 10-20% w/w of the total enzyme protein;
d) the pectate-lyase of the enzyme composition is present at a ratio between 0-10% w/w of the total enzyme protein;
e) the mannanase and/or amylase of the enzyme composition is present at a ratio between 0-10% w/w of the total enzyme protein; and/or
f) the cellulolytic background composition is present in the enzyme composition at a ratio between 40%-99% w/w of the total enzyme protein.

13. The process of claim 1, wherein the enzyme composition further comprises one or more enzymes selected from an additional cellulase, an AA9 polypeptide, a hemicellulase, a cellulose inducible protein (CIP), an esterase, an expansin, a ligninolytic enzyme, an oxidoreductase, a pectinase, a protease, and a swollenin.

14. The process of claim 13, wherein the hemicellulase is one or more enzymes selected from a xylanase, an acetylxylan esterase, a feruloyl esterase, an arabinofuranosidase, a xylosidase, and a glucuronidase.

15. The process of claim 1, wherein the composition comprises the cellulolytic back around composition and: a protease and a lipase; a lipase and a beta-glucanase; or a protease, a lipase, and a beta-glucanase.

16. The process of claim 10, wherein the mannanase is an endo-mannosidase derived from *Bacillus bogoriensis*.

17. The process of claim 11, wherein the amylase is an alpha-amylase derived from *Rhizomucor pusillus*.

18. The process of claim 12, wherein
a) the protease of the enzyme composition is present at a ratio between 5-15% w/w of the total enzymes protein;
b) the lipase of the enzyme composition is present at a ratio between 2.5-7.5% w/w of the total enzyme protein;
c) the beta-glucanase of the enzyme composition is present at a ratio between 10-20% w/w of the total enzyme protein;
d) the pectate-lyase of the enzyme composition is present at a ratio between 2.5-7.5% w/w of the total enzyme protein;
e) the mannanase and/or amylase of the enzyme composition is present at a ratio between 2.6-7.5% w/w of the total enzyme protein; and/or
f) the cellulolytic background composition is present in the enzyme composition at a ratio between 60%-80% w/w of the total enzyme protein.

19. The process of claim 1, wherein
a) the lipase of the enzyme composition is present at a ratio between 2.5-7.5% w/w of the total enzyme protein;
b) the protease of the enzyme composition is present at a ratio between 5-15% w/w of the total enzymes protein; and/or
c) the beta-glucanase of the enzyme composition is present at a ratio between 10-20% w/w of the total enzyme protein.

20. A process for solubilizing Municipal Solid Waste (MSW) comprising:
(a) contacting the MSW with an enzyme composition comprising a cellulolytic background composition present at a ratio between 40-99% w/w of the total enzymes protein in combination with
(i) a protease present at a ratio between 0-20% w/w of the total enzymes protein, wherein the amino acid sequence of the protease has at least 90% sequence identity to SEQ ID NO: 1;
(ii) a lipase present at a ratio between 2.5-7.5% w/w of the total enzymes protein, where in the amino acid sequence of the lipase has at least 90% sequence identity to SEQ ID NO: 2 or SEQ ID NO: 3; and
(iii) a beta-glucanase present at a ratio between 0-30% w/w of the total enzymes protein, wherein the amino acid sequence of the beta-glucanase has at least 90% sequence identity to SEQ ID NO: 4, in order to produce solubilized and/or hydrolysed MSW.

21. The process of claim 20, wherein said lipase comprises SEQ ID NO: 3.

* * * * *

UNITED STATES PATENT AND TRADEMARK OFFICE
CERTIFICATE OF CORRECTION

PATENT NO.       : 11,124,808 B2
APPLICATION NO.  : 15/506881
DATED            : September 21, 2021
INVENTOR(S)      : Hanne Risbjerg Soerensen et al.

Page 1 of 1

It is certified that error appears in the above-identified patent and that said Letters Patent is hereby corrected as shown below:

In the Claims

Claim 15, Column 54, Line 2, "back around" should read --background--

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*